(12) United States Patent
Scholz et al.

(10) Patent No.: US 10,420,957 B2
(45) Date of Patent: Sep. 24, 2019

(54) METHOD FOR DETERMINING AN EFFECT OF A PARTICLE BEAM ON A MATERIAL

(71) Applicant: GSI Helmholtzzentrum fuer Schwerionenforschung GmbH, Darmstadt (DE)

(72) Inventors: Michael Scholz, Erzhausen (DE); Thilo Elsaesser, Buckenhof (DE)

(73) Assignee: GSI HELMHOLTZZENTRUM FUER SCHWERIONENFORSCHUNG GMBH, Darmstadt (DE)

( * ) Notice: Subject to any disclaimer, the term of this patent is extended or adjusted under 35 U.S.C. 154(b) by 256 days.

(21) Appl. No.: 15/331,967

(22) Filed: Oct. 24, 2016

(65) Prior Publication Data

US 2017/0036038 A1   Feb. 9, 2017

Related U.S. Application Data

(63) Continuation of application No. 13/263,102, filed as application No. PCT/EP2010/002495 on Apr. 23, 2010, now abandoned.

(51) Int. Cl.
*A61N 5/10* (2006.01)
*G21K 1/10* (2006.01)
*H01J 37/302* (2006.01)

(52) U.S. Cl.
CPC .......... *A61N 5/1031* (2013.01); *G21K 1/10* (2013.01); *H01J 37/3023* (2013.01);
(Continued)

(58) Field of Classification Search
CPC .................................................. A61N 5/1031
See application file for complete search history.

(56) References Cited

U.S. PATENT DOCUMENTS 4,442,352 A    4/1984  Brahme
5,900,443 A    5/1999  Stinnett et al.
(Continued)

OTHER PUBLICATIONS

Krämer and Scholz, *Treatment planning for heavy-ion radiotherapy: calculation and optimization of biologically effective dose*, Physics in Medicine and Biology, vol. 45, pp. 3319-3330 (Dec. 2000).
(Continued)

*Primary Examiner* — Manuel L Barbee
*Assistant Examiner* — Raymond L Nimox
(74) *Attorney, Agent, or Firm* — Leydig, Voit & Mayer, Ltd.

(57) ABSTRACT

A method for creating a first data set for modifying an irradiation plan parameter data set used for controlling an irradiation system for irradiating a target volume in an irradiation volume using an ion beam includes defining a sensitive volume within the biological material to be irradiated, determining a fluence distribution of the ion beam, determining a microscopic dose distribution of the ion beam, determining, from the microscopic dose distribution of the ion beam, a spatial microscopic damage distribution of the ion beam, determining an expected value for a number of correlated damage events in a sub-micrometer range in the sensitive volume from the spatial microscopic damage distribution of the ion beam in the sensitive volume, determining the effect of the ion beam on the biological material, and storing data that indicate the effect of the ion beam on the material.

21 Claims, 10 Drawing Sheets

(52) U.S. Cl.
CPC ............ *A61N 2005/1034* (2013.01); *A61N 2005/1087* (2013.01); *H01J 2237/316* (2013.01)

(56) References Cited

U.S. PATENT DOCUMENTS

| | | | |
|---|---|---|---|
| 6,301,329 | B1 | 10/2001 | Surridge |
| 6,787,771 | B2* | 9/2004 | Bashkirov ............ G01N 27/64 250/287 |
| 6,789,022 | B2 | 9/2004 | Sutherland |
| 8,053,736 | B2* | 11/2011 | Ahnesjo ............ G01T 1/02 250/370.07 |
| 8,299,448 | B2 | 10/2012 | Bert et al. |
| 2004/0000650 | A1 | 1/2004 | Yanagisawa et al. |
| 2007/0034812 | A1* | 2/2007 | Ma ............ A61N 5/1031 250/492.21 |
| 2007/0181815 | A1* | 8/2007 | Ebstein ............ G01T 1/02 250/370.11 |
| 2008/0067405 | A1 | 3/2008 | Nihongi et al. |
| 2008/0071131 | A1 | 3/2008 | Rietzel et al. |
| 2008/0118966 | A1 | 5/2008 | Chang et al. |
| 2010/0012859 | A1 | 1/2010 | Claereboudt |
| 2010/0108903 | A1 | 5/2010 | Bert et al. |
| 2010/0301235 | A1* | 12/2010 | Bert ............ A61N 5/103 250/492.3 |
| 2010/0327188 | A1 | 12/2010 | Bert et al. |
| 2012/0025076 | A1 | 2/2012 | Kraft |

OTHER PUBLICATIONS

Scholz et al., *Computation of cell survival in heavy ion beams for therapy*, Radiation Environmental Biophysics, vol. 36, pp. 59-66 (,Dec. 1997).

Lem II: Elsässer and Scholz, *Cluster effects within the local effect model*, Radiation Research vol. 167, 319-329 (2007).

Wroe A J et al. *Nanodosimetric cluster size distributions of therapeutic proton beams*, IEEE Transactions on Nuclear Science, New York, NY, vol. 53, Nr:2, pp. 532-538 (Dec. 2006).

Sato Tatsuhiko et al. *Biological dose estimation for charged-particle therapy using an improved PHITS code coupled with a microdosimetric kinetic model*, Radiation Research, Academic Press Inc, US vol. 171, Nr:1, pp. 107-117 (Dec. 2009).

Andrey V Solovyov, *Physics of ion beam cancer therapy: A multiscale approach*, Physical Review E (Statistical, Nonlinear, and Soft Matter Physics), College Park, MD vol. 79, pp. 11909-1- 11909-7 (Dec. 2009).

Semenenko and Stewart, *Fast Monte Carlo simulation of DNA damage formed by electrons and light ions*, Physics in Medicine and Biology, London, GB, vol. 51, Nr:7, pp. 1693-1706 (Dec. 2006).

European Patent Office, International Search Report in International Patent Application No. PCT/EP2010/002495 (dated Sep. 2, 2010).

Krämer and Scholz, *Radiation Calculation of biological effects in ion radiotherapy*, Physics in Medicine and Biology, vol. 51, pp. 1959-1970 (, Dec. 2006).

Briden, P., Hold, P., Simmons, J.: *The track structures of ionizing particles and their application to radiation biophysics*. Radiat. Environ. Biophys. vol. 38, p. 175-184, Dec. 1999.

Elsässer, T., *Accuracy Of The Local Effect Model For The Prediction Of Biologic Effects Of Carbon Ion Beams In Vitro And In Vivo*, Int. J. Radiation Oncology Biol. Phys., vol. 71, No. 3, pp. 866-872, Dec. 2008.

Furosawa et al. 2000, *Inactivation of Aerobic and Hypoxic Cells from Three Different Cell Lines by Accelerated 3He-, 12C- and 20Ne-Ion Beams*, Radiation Research, vol. 154, pp. 485-496, Dec. 2000.

Gemmel, A. et al., *Biological dose optimization with multiple ion fields*, Phys. Med. Biol., 53 (23), p. 6991-7012, Dec. 2008.

Elsässer, T., *Vergleich des Local-Effects-Modells (LEM) mit aktuellen experimentellen in-vivo and in-vitro Daten*, GBS-Tagung, Braunschweig, p. 1, Dec. 2006.

Hada, M., Georgakilas, A, *Formulation of Clustered DNA Damage after High-LET Irradiation*, A review in J. Radiat. Res., vol. 49, p. 203-210, Dec. 2008.

Judas, L., Lokajicek, M., *Cell inactivation by ionizing particles and the shapes of survival curves*, J. theor. Biol., vol. 210, p. 15-21, Dec. 2001.

* cited by examiner

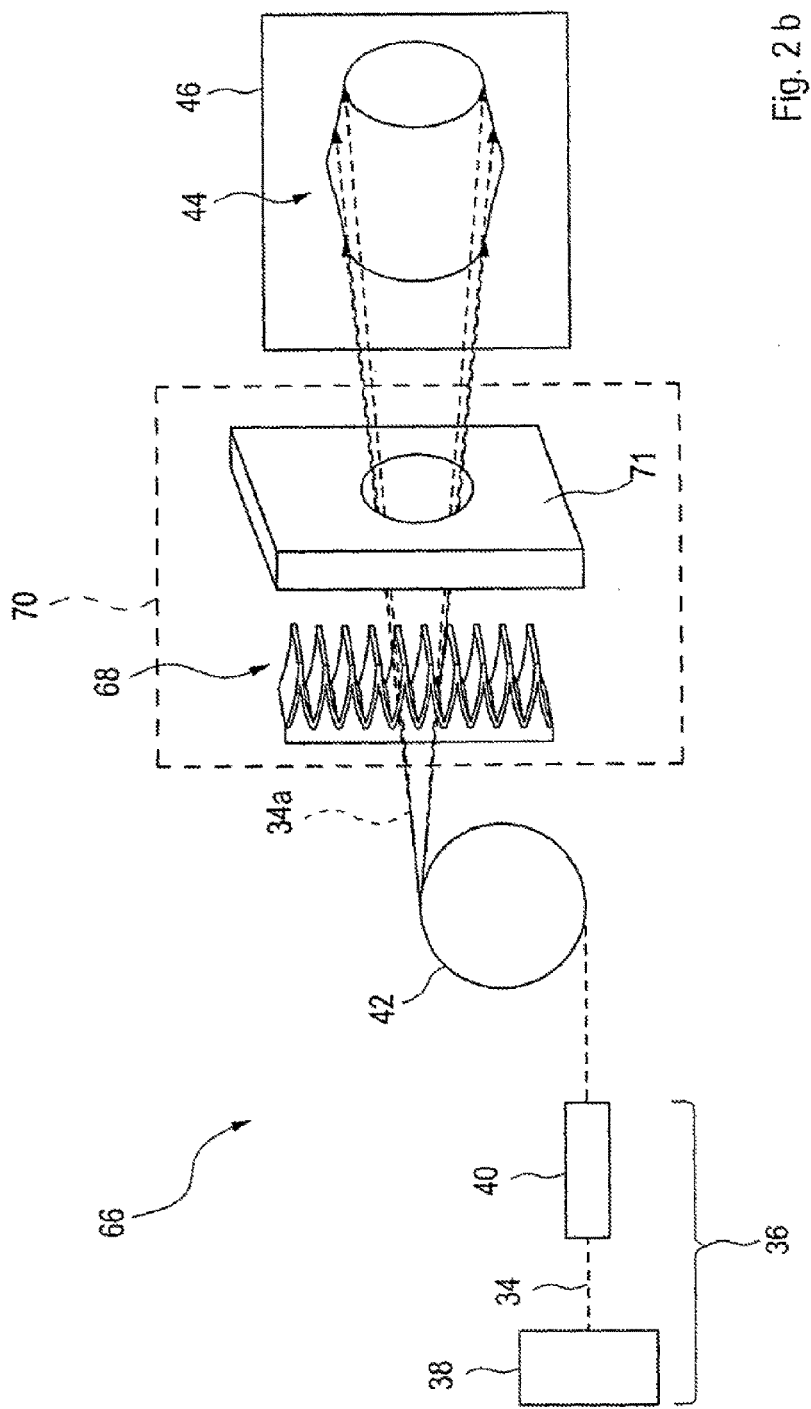

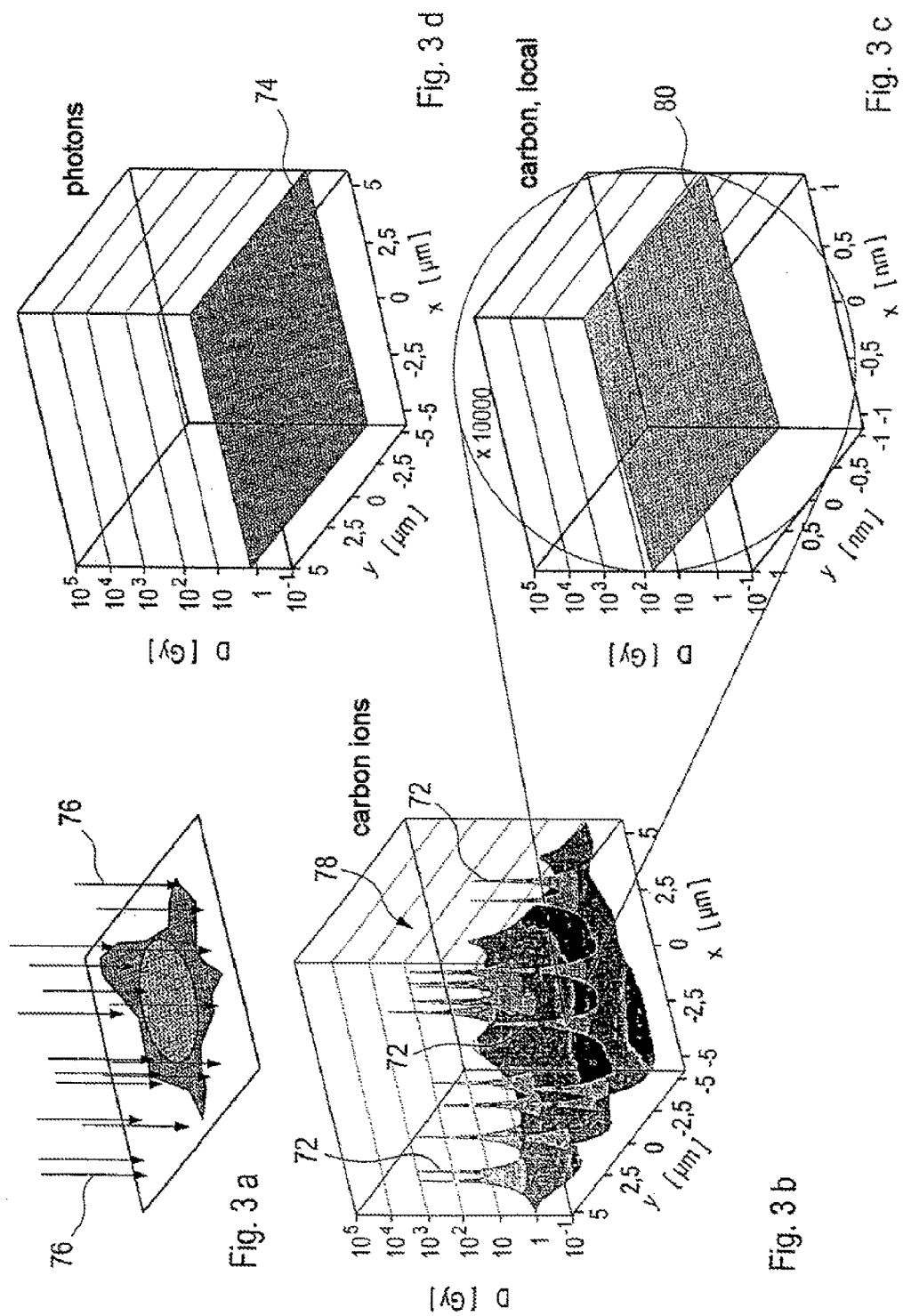

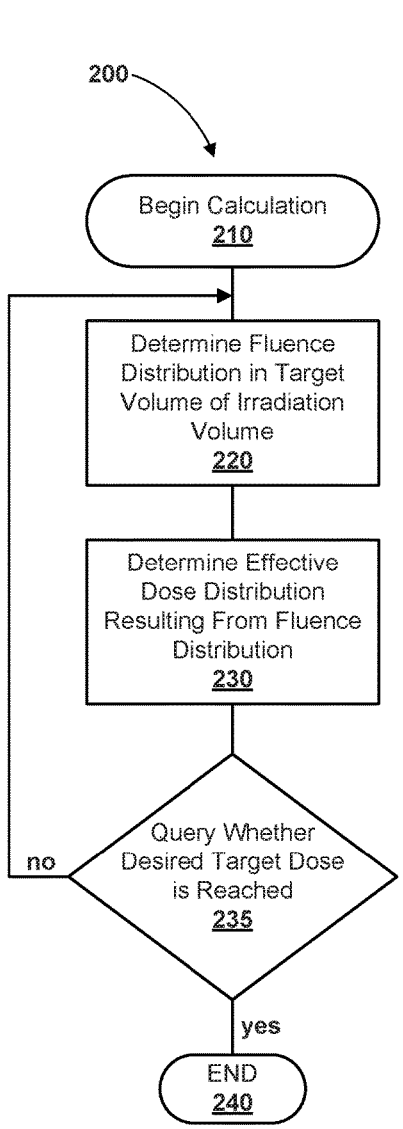
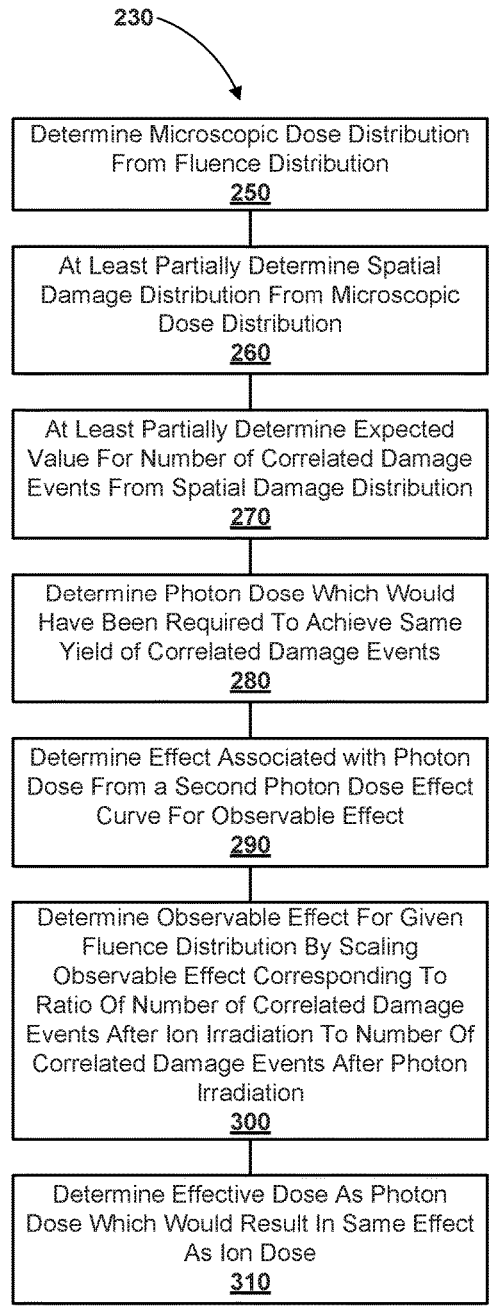
Fig. 4
Fig. 5

METHOD FOR DETERMINING AN EFFECT OF A PARTICLE BEAM ON A MATERIAL

CROSS-REFERENCE TO PRIOR APPLICATIONS

This application is a continuation of U.S. patent application Ser. No. 13/263,102, filed on Oct. 6, 2011, which is a U.S. National Phase application under 35 U.S.C. § 371 of International Application No. PCT/EP2010/002495, filed on Apr. 23, 2010 and published as WO 2010/121822, and claims benefit to German Patent Application Nos. DE 10 2009 018 545.3, filed on Apr. 24, 2009 and DE 10 2009 031 772.4, filed Jun. 28, 2009. The entire disclosures of all of the foregoing applications are hereby incorporated by reference in their entireties herein.

FIELD

The invention relates to a method for determining an action of a particle beam on a material which is at least partially irradiated or to be irradiated, a method for irradiation planning for a target volume, and a method for irradiating a target volume with a particle beam, an irradiation plan, a beam modification facility and an irradiation device.

BACKGROUND

Irradiation of a target volume in an irradiation volume with ion or particle beams concerns the irradiation of matter, in particular inorganic, organic and biological materials, and is used in various fields of research, industry and medical engineering. The target volume includes, in particular, the region in which a predetermined dose is to be deposited in order to modify the irradiated material; the irradiation volume also includes, in particular, those regions of the material which are penetrated by radiation in order to achieve the desired dose in the target volume. A particle beam or ion beam is understood, in particular, as a high-energy beam of either charged particles, e.g. protons, carbon ions or ions of other elements, pions or neutral particles, e.g. neutrons. In the following description, the terms ion beam and particle beam are used interchangeably. High energy is understood, in particular, as energy of the particles in the region of several MeV/amu up to several GeV/amu (amu: atomic mass unit).

An irradiation device which is suitable for carrying out the irradiation in general has an acceleration facility which generates and forms the ion beam, the ion beam being guided for the irradiation via a beam transport system into a region in which the irradiation volume is arranged. The irradiation device also includes a beam modification facility, which can adapt the parameters of the ion beam to the position and size of the target volume.

The irradiation volume can, for example, be a detector system, which is used to verify an irradiation field. In general, the irradiation volume includes an irradiation field, which is a field with maximum extent in the lateral direction, in general in the x and y directions, and is perpendicular to the direction of the ion beam. The detector system can consist of a detector field or a so-called stack, with multiple laterally extended detector fields arranged one behind the other. In the dosimetry field, for example, films with a photographic emulsion are used for this purpose. Nuclear trace detectors are also used to measure the fluence distribution in the irradiation field. In the field of medical applications, irradiation of biological tissue is used to study the action of particle radiation, in order to be able to estimate the action of exposure to beams of cosmic radiation in space. Finally, the irradiation volume can also be the volume of a tumour in a patient. In this case, ion beams are used to destroy tumour tissue in the target volume.

In tumour therapy, the special properties of ion beams make it possible to destroy the tumour tissue with minimal damage to the surrounding healthy tissue. This is associated with the favourable depth dose distribution of ion beams. When high-energy ion beams penetrate the material, at first they deposit little energy. With increasing depth, the energy deposition increases, reaches its maximum in the region of a distribution curve called the Bragg peak, and then falls steeply. In this way, even in the case of deeper tumours, more energy can be deposited in the tumour tissue than in the surrounding healthy tissue.

Ion beams have an action on the irradiation volume depending on the type of material to be irradiated and the parameters of the ion beam. In general, ion beams have a different action from photon radiation. This means that with ion beams the dose to be deposited is different from with photon beams, in order to achieve a predetermined action or predetermined irradiation effect. The photon dose $D_\gamma$ which would cause the same irradiation effect as the ion dose $D_I$ is designated as the effective dose. The changed action of ion beams is observed for inorganic, organic and biological material. In inorganic materials, a smaller action of ion beams compared with photon beams tends to be observed. In contrast, when biological material is irradiated with ions, usually a higher action and thus a greater effect compared with photon irradiation is observed.

Before the actual irradiation, in general an irradiation plan for irradiating the target volume, e.g. a sub-region in a phantom or tumour, is produced. In the case of irradiation with ion beams, this irradiation plan should take into account as far as possible the action of ion beams.

Various methods for producing an irradiation plan are known. For example, in the publication Krämer and Scholz 2000, Physics in Medicine and Biology, Vol. 45, pp. 3319-3330, a method for producing an irradiation plan is described.

The action of ion beams in the material depends in a complex manner on the ion type, the ion energy, the irradiation dose, the irradiated material and the observed effect in each case. Experimental determination of these multiple dependencies with the necessary precision for irradiation planning is unachievable in practice. Models which allow prediction of the changed effectiveness therefore represent an important tool for implementation of irradiation planning. These models are usually based on simplifications and approximations, since the mechanisms on which they are based for damaging inorganic, organic and biological material are not yet clarified quantitatively with sufficient precision. Correspondingly, in general the application field of the models is also limited.

An example of such a model is described in the publication Scholz et al., Radiation Environmental Biophysics, Vol. 36, pp. 59-66 (1997). The model is called LEM, which is an abbreviation of "local effect model".

The models until now cannot supply any sufficiently precise information for irradiation planning over the whole range from light to heavy ions.

SUMMARY

In an embodiment, the present invention provides a method for creating, at a computer readable memory, a first data set for modifying an irradiation plan parameter data used for controlling, directly or indirectly, an irradiation system for irradiating a target volume in an irradiation volume using an ion beam, wherein the first data set accounts for an effect of an ion beam on a biological material, and wherein the effect of the ion beam on the biological material involves the induction of damage events in the biological material. The method includes defining a sensitive volume within the biological material to be irradiated, determining a fluence distribution of the ion beam, determining a microscopic dose distribution of the ion beam from the fluence distribution of the ion beam, determining, from the microscopic dose distribution of the ion beam, a spatial microscopic damage distribution of the ion beam in the sensitive volume which is deduced from a first photon dose effect curve that describes a number of damage events per dose unit, determining an expected value for a number of correlated damage events in a sub-micrometer range in the sensitive volume from the spatial microscopic damage distribution of the ion beam in the sensitive volume, wherein correlated damage events are combinations of individual damage events within a specified distance, determining, using the expected value of the number of correlated damage events in a sub-micrometer range in the sensitive volume, the effect of the ion beam on the biological material, and storing, at the computer readable memory unit, data that indicate the effect of the ion beam on the material.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following:

FIGS. 3a-3d are schematic representations of a microscopic dose distribution in a sensitive volume for irradiation with ions (3a, 3b, 3c) and with photons (3d);

FIG. 4 is a flowchart of a method for irradiating a target volume;

FIG. 5 is a flowchart of method steps which can be executed in more detail in the method shown in FIG. 4;

FIG. 9a is a schematic representation of an irradiation dose applied with helium ions in a target volume, as a function of the penetration depth;

FIG. 9b is a representation of cell survival as a function of penetration depth in a target volume, after irradiation with the irradiation field from FIG. 9a;

FIG. 10a is a schematic representation of an irradiation dose applied with protons and carbon ions, in a target volume for the case of a typical two-field irradiation;

FIG. 10b is a schematic representation of the calculated cell survival and the associated experimentally determined survival probabilities for irradiation of a target volume with the irradiation fields from 10a.

DETAILED DESCRIPTION

Figure 1:
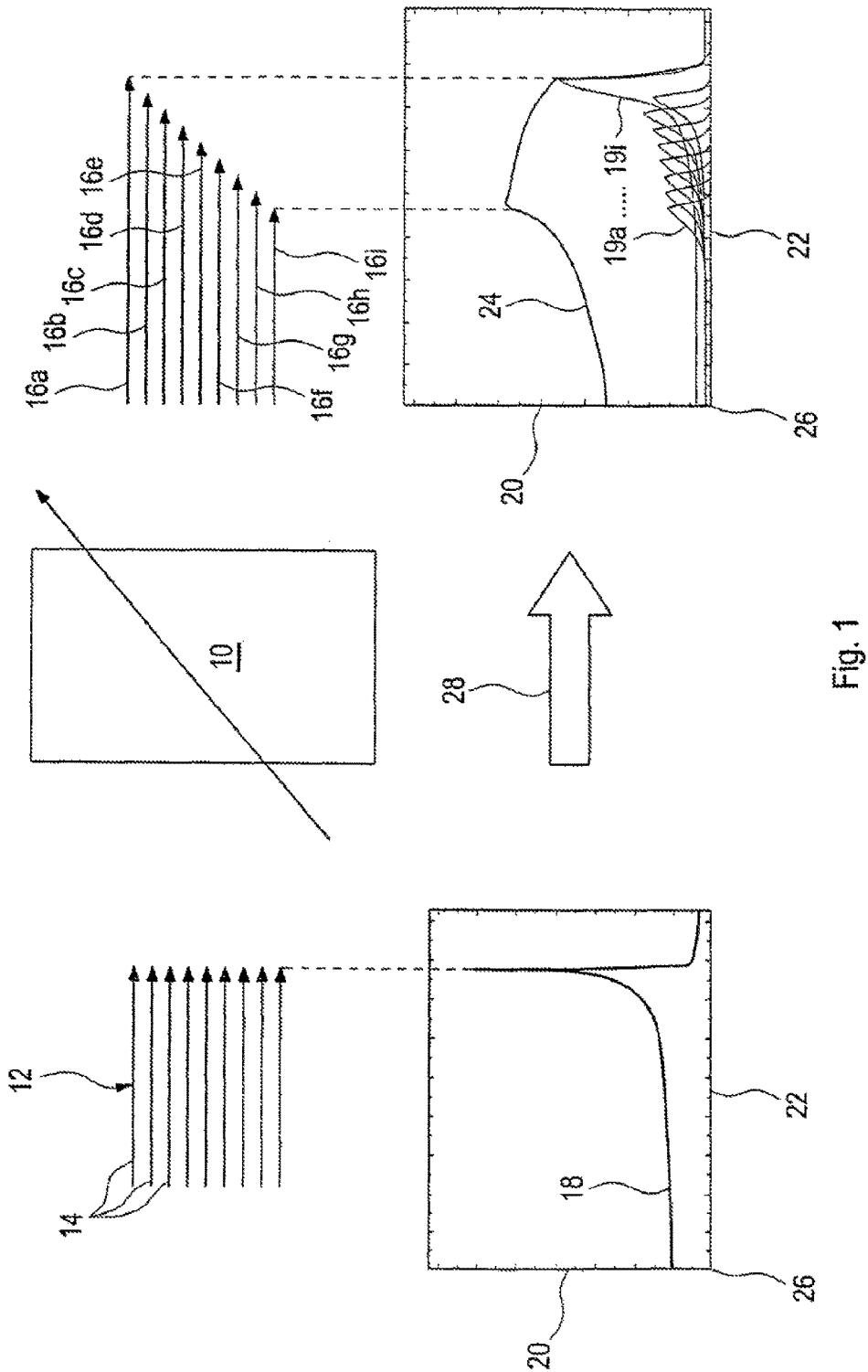
FIG. 1 is a schematic representation of a functional principle of a beam modification facility, and its action on a depth dose distribution.

It is advantageous to describe and predict the action of particle beams, in particular ion beams, using a model over a wide range of masses, in particular from protons to neon ions, reliably with the required precision.

In an embodiment, the present invention provides an improved method compared with the prior art for determining the action of a particle beam on a material which is to be irradiated or is irradiated. The intention is also to create a method for irradiation planning for a target volume and for irradiating a target volume, and to create an improved irradiation device.

In an embodiment of the proposed method, an action of a particle beam on a material which is to be irradiated or is irradiated at least partially is determined. From at least one parameter which characterises the particle beam and at least one parameter which characterises the material properties, the action of the particle beam in the material is at least partially determined on the basis of a microscopic damage correlation.

The microscopic damage correlation is understood, in particular, as spatial interaction of damage or damage events which have occurred in the material, preferably on a length scale. The size of the length scale which is used is preferably according to an order of magnitude which is meaningful for the material, the damage which has occurred, and their spatial interaction. This length scale can be different according to the material which is to be irradiated or is irradiated, in particular of different size. The damage correlation of the damage for an inorganic material can thus differ from the damage in a biological material.

The action of the particle beam on the material is typically influenced by the features of the particle beam, e.g. the energy, the ion type and/or the linear energy transfer of the particle beam in the material (linear energy transfer: LET). In other words, the action of the particle beam depends, among other things, on the energy of the particle beam, the mass and charge state of the individual particle in the particle beam, and the particle beam energy which is transferred to the material. A typical energy for a particle beam is in the range of several hundred keV GeV/amu to several tens of GeV/amu, where "amu" means "atomic mass unit".

In general, the material property describes a property of the material, and concerns a sensitivity of the material to an energy input which concerns an energy deposition and thus a dose which is deposited in the material. A damage event can be induced by the energy input, so that the sensitivity describes the energy deposition which is necessary to induce a damage event. This can be the sensitivity of a polymer material, the sensitivity of an X-ray film or the sensitivity of biological tissue. This sensitivity of the material is typically determined and measured for irradiation of a material with photon radiation, and is thus a material property.

In an embodiment of the invention, the microscopic damage correlation can take place in the sub-micrometer range. In particular in the case that the material is a biological material, the length scale is in the sub-micrometer range. The sub-micrometer range includes a length range of a few hundred nanometers, in particular greater than approximately 100 nm. Preferably, the length scale includes a range between approximately 400 and 500 nm, particularly preferably 440 nm. In principle, the damage or damage events can be changes in the material or components of the material resulting from the energy loss in the material. This change can be a chemical change of a chemical compound, e.g. the disintegration of inorganic or organic molecules, the break in a polymer chain, the elimination of side chains or side groups in a polymer material, and/or one or more single strand breaks or double strand breaks of the DNA in a biological material. In other words, the damage or damage events induced by the particle beam can be put into a spatial relationship to each other, preferably all damage or damage events which occur or are to be expected being observed on a length scale of about 100 nm or greater, but less than about 1000 nm. In particular, in biological material, e.g. in cells or tissues composed of cells, the DNA double strand breaks which occur or are to be expected can be observed at a distance of about 440 nm, and used as the characteristic magnitude for the action of the particle beam on the material. In this case the resolution of the length scale can preferably be less than the length scale, in particular in the region of about 10 nm.

In an embodiment, the microscopic damage correlation can be determined using a spatial microscopic damage distribution. Additionally, the spatial microscopic damage distribution can be determined at least partially from a microscopic dose distribution. Thus the microscopic damage distribution which is generated by the particle beam can be determined, the probability of local damage being induced being deduced at least partially from a first photon dose effect curve which describes the number of damage events per dose unit. Additionally, according to an embodiment of the invention, when the microscopic damage correlation is determined an expected value for a number of correlated damage events in a suitably chosen partial volume of a sensitive volume can be at least partially determined from the spatial, microscopic damage distribution, in particular the ratio of the number of correlated damage events and the dose deposited by the particle beam, and thus the total number of induced, isolated and correlated damage events. Additionally, a photon dose which would have been necessary to achieve the same yield of correlated damage events corresponding to the expected value of the number of correlated damage events for the particle beam can be determined. In this case, the yield of correlated damage events can describe the ratio of the number of correlated damage events and the dose deposited by the irradiation. Alternatively, the yield of correlated damage events can also describe the ratio of the number of correlated damage events and the number of isolated damage events. According to an embodiment of the method, an effect associated with this photon dose can at least partially be determined from a second photon dose effect curve. The action of the particle beam can at least partially be determined by scaling the effect associated with the photon dose corresponding to the ratio of the photon dose and a dose which is deposited in the sensitive volume by the particle beam. Preferably, the action of the particle beam can at least partially be determined by scaling the effect associated with the photon dose corresponding to the number of correlated damage events and the number of correlated damage events induced by ion irradiation.

The terms used in the method steps to specify the action of a particle beam on a material will be explained in more detail below.

In an embodiment, the spatial, microscopic damage distribution (rSv) can in general be determined by a spatial distribution of the damage or damage events. The spatial, microscopic damage distribution can at least partially be determined from the microscopic dose distribution (mDv).

In an embodiment, the microscopic dose distribution, in particular the local dose distribution, can be determined with at least partial use of the radial dose distribution around a single ion trace. The radial dose distribution describes the expected value of the local energy deposition as a function of the distance from the trajectory of the ion trace. The advantage of using the radial dose distribution is that in this way it is possible to refer directly to the effects after photon irradiation. The radial dose distribution can be calculated by Monte Carlo simulations, for example. Another possibility can be given by analytical dose description in the sense of an amorphous path structure.

The photon dose effect curves are usually determined experimentally. For example, the mean number of damage events can often be described by a linear-quadratic relation:

$$N_{damage} = \gamma D_x + \delta D_x \quad (1)$$

where $D_x$ is the X-ray or photon dose, and $\gamma$ and $\delta$ are material-specific constants such as parameters to describe the number of polymerisation events per dose unit in a monomer crystal of a GafChromic film, or parameters for the number of double strand breaks per dose unit.

The action of photon beams is characterised in that the spatial distribution of the occurring damage events is in general distributed uniformly stochastically on the basis of the physical properties of the energy deposition of photons. If the sensitive volume is divided into partial volumes, which are also called parcels, it can be assumed that each parcel has the same damage density distribution. This means that a uniform damage distribution exists in each parcel.

In contrast, for a sensitive volume which is divided into parcels and irradiated with ions, because of the extremely localised energy deposition of ion beams a heterogeneous damage distribution is present. If the sensitive volume is divided into parcels of a size less than, or less than or equal to, $1 \times 1 \times 1$ nm$^3$ ($\leq 1 \times 1 \times 1$ nm$^3$), and in each parcel the microscopic dose, in particular the local microscopic dose distribution, is determined, a microscopic, spatial damage distribution rSv can thus be determined.

In an embodiment, the expected value for the number of correlated damage events (AkS) in a suitably chosen partial volume of a sensitive volume can be determined more precisely at least partially from the spatial, microscopic damage distribution. In this case the term "correlated damage event" means damage which can occur through the spatial interaction of individual damage events. The spatial correlation can thus be defined by analysing the distances between the individual damage events. In the case of biological material, for example, a correlated damage event can be given by the combination of two double strand breaks, which results in damage which is more difficult for the biological material to repair. The advantage of using correlated damage events is that in this way, in particular, the non-linear reaction of materials or cells to irradiation can be better taken into account.

In an embodiment, a photon dose (PD1) which would have been necessary in order to achieve the same yield of correlated damage events as after ion irradiation, i.e. the same number of correlated damage events (AkS) relative to the total number of individual damage events or the number of isolated damage events (AiS), can be determined. This means that for a macroscopic photon dose within the irradiation field, a spatial distribution of damage events, their type and their number is determined according to the photon dose effect curve PEK1, from which the expected value of the number of correlated damage events can be determined. In particular, the result is thus a photon dose PD1 which results in the same yield of correlated damage events as after ion radiation. For example, for the expected value of the number of double strand break pairs within a specified distance, it can be assumed that this depends quadratically on the macroscopic photon dose. In particular, this makes rapid determination of PD1 possible on the basis of simulation of the yield of correlated damage events at a specified photon dose. For this purpose, it is assumed that with parcels which are chosen to be sufficiently small and with equal local dose, the same damage is induced with photon and ion irradiation. The reason for this can also be that with a sufficiently small parcel volume, even in the case of ion beams, the expected value of the energy deposition in this volume can be assumed to be homogeneously distributed, and can thus be compared directly with the action of irradiation of photon beams. In this case, it is advantageous that the number of damage events which are known from photon irradiation can be transferred in this dimension to a material irradiated with ions.

In an embodiment, from a second photon dose effect curve for the observable effect (PEK2), an effect (E1) associated with the photon dose (PD1) can at least partially be determined. In contrast to the photon dose effect curve (PEK1), which describes the local, microscopic or molecular damage, the photon dose effect curve (PEK2) represents the macroscopically observable effect. For example, in the case of cells, PEK2 can describe the inactivation of cells, e.g. characterised by the linear-quadratic parameters $\alpha_x$ and $\beta_x$, which are known for many cell and tissue types. In the case of tissues or organs, PEK2 can describe the probability of tissue damage or organ failure. Similarly to PEK1, there is an advantage in that by reference to the experimental photon data, with PEK2 high precision of the determined biological effects for ion irradiation can be achieved. Additionally, with this method, compared with other methods, the computation times can be drastically reduced.

In an embodiment, the observable effect (E2) can at least partially be determined from the scaling of the biologically relevant effect (E1) corresponding to the ratio of the photon dose (PD1) and the ion dose (ID) deposited in the sensitive volume. In particular, the observable effect (E2) can be calculated as follows:

$$E2 = E1 \cdot \frac{AkS_2}{AkS_1} \quad (2)$$

where it can be assumed, for example, that E2 is produced by a single ion with associated ion dose deposition ID and associated photon dose PD1. It can also be assumed, for example, that E2 is produced by a single ion, and AkS1 and AkS2 describe the number of correlated damage events by the photon dose PD1 and ion dose ID respectively.

In an embodiment, the action of the particle beam can also be determined directly from the number of isolated and correlated damage events, if the effect of these damage types can be deduced from the photon dose effect curve:

$$E2 = AiS2 \cdot \epsilon_i + AkS2 \cdot \epsilon_k \quad (3)$$

In an embodiment, the effective dose can be at least partially determined from the photon dose (PD2) associated with the observable effect (E2). Thus by suitable optimisation methods, the ion dose for each point of an irradiation field can be chosen so that in this way a specified effect can be achieved at every point of the irradiation volume. In the case of a mixed beam field, for example, PD2 can also be determined by observing the beam field at every point of the irradiation field according to the methods which are known in the prior art. In this case, in particular, the so-called intrinsic RBW of individual ions can be used, it being possible to determine the intrinsic RBW as follows:

$$RBW_{int} = \frac{\alpha_{int}}{\alpha_X} = \frac{E2_{single}}{ID_{single} \cdot \alpha_X} \quad (4)$$

where $\alpha_{int}*ID_{single}$ corresponds to the biological effect $E2_{single}$ of a single ion with dose deposition $ID_{single}$. According to the publication Kramer and Scholz, Physics in Medicine and Biology, Vol. 51, pp. 1959-1970, 2006, $\beta_{int}$ can be obtained from $\alpha_{int}$ and from $\alpha_{int}$ and $\beta_{int}$ finally the effect E2 for the whole mixed beam field can be obtained. The effect after ion irradiation can thus be described, for example, by means of the linear-quadratic parameters $\alpha_{ion}$ and $\beta_{ion}$.

"Determine" above can be understood, in particular, as meaning that the respective magnitudes are calculated in a computation unit in a complex technical method.

An advantage of the method for determining the action of a particle beam in or on a material can be seen in that it allows direct transfer of experience with conventional irradiation to irradiation with particle beams. A further advantage of the proposed method is that the $RBW_{int}$ values and/or linear, quadratic coefficients can be calculated in advance for individual ions from protons to neon and for energies from 0.1 MeV/u to 1 GeV/u, independently of the existing beam field, and stored in the form of tables, before E2 is calculated for the mixed beam field. This can result in a further considerable saving of computation time.

Further advantages and properties of these developments are given analogously in the following description of the method for irradiation planning, and/or of the method for irradiating a target volume, and of the irradiation device and its developments.

In an embodiment, the proposed method for irradiation planning for a target volume with a particle beam has the following steps:—specifying a target volume in the irradiation volume; —determining a fluence and/or energy distribution of the particle beam within an irradiation volume which includes the target volume; —determining an effective dose distribution resulting from the fluence and/or energy distribution, data which determine the action on the material of the irradiation volume at least partially on the basis of a microscopic damage correlation being used. In this case, the method step of specifying a target volume in an irradiation volume can precede the determination of a fluence and/or energy distribution.

In an embodiment of the invention, typically for a fluence and/or energy distribution of a particle beam, the action generated in the target volume is determined, the effective dose distribution preferably being determined. The determination of the action is preferably based on the microscopic damage correlation. This denotes an interaction of the damage events on a sub-micrometer scale, which is preferably greater than approximately 100 nm.

In this case the target volume is usually a volume to be irradiated in an object. The object can be a delimited volume in a material to be irradiated, e.g. a detector system, an X-ray film, a phantom to simulate an irradiation situation, or a person. The irradiation volume can be the target volume, the material arranged in front of the target volume, and also the material arranged after the target volume, seen in the direction of the particle beams. In this case the material of the target volume, e.g. the material to be modified of an object or the tumour to be destroyed, is usually in the region of the Bragg peak of the particle beam.

The fluence distribution, which usually describes the number of ions or particles passing through per unit area (ions/cm$^2$) and the associated energy distribution, is usually determined at at least one point of the target volume, but preferably in a three-dimensional (3D) arrangement or matrix of points of the target volume. The fluence distribution can include, as well as information about the primary ion beams, information about the secondary particles generated by nuclear reactions.

From the fluence and energy distribution, a resulting macroscopic, physical dose distribution can be determined. The macroscopic, physical dose distribution is understood below as the dose distribution which results from the expected value of the dose deposition of the particle beams in volumes of typically several cubic millimeters or greater. This dose distribution is based on the knowledge of the number of particles and their energy deposition at each point $x_i$, $y_i$, $z_i$ of the target volume.

However, for describing the irradiation effect to be expected, in the case of ion or particle beams the macroscopic dose distribution alone is insufficient. The beam action is also decisively determined by the changed effectiveness of ion beams compared with conventional photon beams.

The aim of irradiation planning is usually to be able to determine the effective dose with a precision of approximately 5 to 10%. The effective dose designates the dose which would have to be deposited with photon beams in order to achieve the same effect as with ion beams. The starting point for calculating the irradiation plan is therefore either the achieved and observable or the desired action or the desired effect on the material of the target volume. In this case parameters of the ion beams to be applied, e.g. ion beam type, ion beam energies and/or usually the changed effectiveness compared with photon beams are used, and from them the dose to be applied is determined or calculated with reference to the target volume.

The LEM according to the prior art makes it possible to deduce the effectiveness of ion beams from knowledge of the physical properties of ion beams and knowledge of the reaction of materials to photon radiation. However, because of the simplifications and approximations which are used, the precision of the model is usually sufficiently precise for irradiation planning only for applications with heavier ions, e.g. carbon. Starting from the original implementation (LEM I), it was possible to improve the precision of the computation by developments (LEM II: Elsässer and Scholz 2007, Radiation Research Vol. 167, 319-329; LEM III: Elsässer et al. 2008, International Journal of Radiation Oncology Biology Physics, Vol. 71, 866-872); however, the model still offers insufficient precision for general application over a broad mass range of ions (protons to neon ions) and energy range (1 MeV/u to 1 GeV/u).

In contrast to the methods used until now in the LEM I to LEM III models, in the case of the proposed method the microscopic spatial damage correlation is used to determine the effective dose. For irradiation of non-biological, e.g. inorganic material, in order to determine the changed effectiveness and thus the effective dose, in particular material constants such as, for example, the sensitivity of silver bromide crystals in X-ray films or the colouring of radiochromic dyes after irradiation are decisive. In the case of irradiation of biological material, e.g. tumour cells, damage to the DNA contained in the cell nucleus usually represents the decisive cause of the observable beam actions. To describe the effective dose, here the relative biological effectiveness (RBW) of the ions is often used. It is defined by the ratio of the ion doses which are necessary to achieve the same effect with photon beams and ion beams.

$$RBW = \frac{D_{Photon}}{D_{Ion}}\bigg|_{Isoeffect} \quad (5)$$

The term isoeffect denotes the same effect for $D_{Photon}$ and $D_{Ion}$. This means that first the damage type or observable effect must be defined and used as a parameter.

In a version of the method for irradiation planning, for various parameters which characterise the particle beam and/or various properties of the material, the effect of the particle beam on the material to be irradiated can be determined on the basis of the microscopic damage correlation in each case. The effects which are determined for the various parameters of the particle beam and for the various material properties, and/or the data and values which characterise the effects, can be held in a memory unit in each case.

In this way, for various properties of the particle beam, e.g. for ions from protons to neon, and/or for energies from 0.1 MeV/u to 1 GeV/u, effects can be calculated in advance and held in a memory unit, e.g. a data set and/or a data table. The stored effects can then be used in a method for irradiation planning.

In order to be able to determine the required dose to achieve the specified effect, the corresponding material constants or the necessary data for describing the relative biological effectiveness, the linear and/or quadratic coefficients of the dose effect curves or other coefficients can preferably be used in the form of a data set or a table containing the data.

Examples of such data sets are tables with parameters for specified ion energies and ion types, which make it possible to determine the relevant RBW values. The data set containing these tables can be designated as an RBW data set, and can be present in the form of a parameter table which is used to control an irradiation device. However, it is also conceivable to implement the method for determining the RBW data set directly in a control facility of an irradiation device. The data set can be present as a parameter field in a control facility to control an irradiation device, e.g. an accelerator.

Additionally, from the fluence distribution the local dose distribution in an irradiation field can be determined at every point in a volume of typically 10×10×10 μm$^3$, with a resolution of typically <1 nm$^3$, i.e. in the sub-nanometer range. The local dose distribution can also take into account the spectral distribution of the particles. The local dose distribution is accordingly a microscopic dose distribution, in contrast to the macroscopic dose distribution defined above.

Determining the action of the particle beam on a material or an effective dose distribution, e.g. in the context of irradiation planning, can be based on taking into account a local damage correlation, which can be determined using the local, microscopic dose distribution. The probability of generating correlated damage events, in particular spatially correlated damage events, depends among other things on the number of damage events in a partial volume of a suitably chosen sensitive volume. In the case of films, the sensitive volume can be defined by the volume of a silver bromide grain; in the case of cells, it can be the cell nucleus. Those damage events which result from interaction of individual damage events within a suitably chosen distance are called correlated damage events. Polymerisation events in a monomer crystal of a GafChromic film, or DNA damage events in a cell nucleus of a biological tissue, can be seen as examples of individual damage events. The probability of generating correlated damage events can accordingly be determined from a distance analysis of the damage events, for example. A simple example of determining correlated biological damage events is calculating the number of double strand break pairs (DSB pairs) within a specified distance.

In the case of prior methods, the number and spatial distribution of the produced damage events is not usually calculated on a (sub-) nanometer scale but rather in the micrometer dimension. The calculation is thus in general based on global information about the energy deposition over the corresponding micrometer ranges; in this way the physical dose deposition which is actually located on the (sub-) nanometer scale in the irradiation field is oversimplified. Additionally, the prior methods are not usually based on transferring the effects from the photon dose effect curve.

The combination of precise calculation of the spatial damage distribution (rSv) in the sub-micrometer range with reference to the photon dose effect curve represents an essential innovation of the method proposed here.

The advantage of this method for irradiation planning is, in particular, that with it a more precise calculation of the effective dose is possible, and thus the irradiation planning can be carried out with significantly improved precision. In particular, the method improves the precision in the case of light ions, so that the proposed method can be used with the same precision over a large range of ions from protons to heavy ions, e.g. neon ions. Additionally, with it the action of ion beams can be taken into account both prospectively for irradiation planning and retrospectively for recalculation, checking and validation of previously created and applied irradiation plans.

In an embodiment, the method can also be used to determine the effectiveness of neutron beams. When a target volume is irradiated with neutrons, charged secondary particles can be generated by nuclear reactions. These in turn cause damage in the sensitive volume. The action of the neutrons is based on the action of the so-called "recoils" which are produced, and is thus characterised by a mixed particle field, which can typically contain charged particles from protons to oxygen ions. To calculate the action of this mixed beam field, therefore, the same methods can be used, similarly to the situation in ion beam therapy.

What is said above also applies to other particles.

In a version of the invention, the method is used to produce an irradiation plan for the target volume, and/or to validate an irradiation plan. The irradiation plan is usually determined before the actual irradiation of a target volume, by calculating a parameter data set, which can be stored in an irradiation device for controlling the irradiation method. Consequently, the irradiation plan comprises parameter data sets which are held in a memory unit in the form of a data set or value table, and which are used directly or indirectly to control an irradiation system, in order to implement the irradiation plan during irradiation. The irradiation plan can ensure that the desired effective dose is applied in the target volume. Because in the determined effective dose distribution, data which depend on the specific beam reactions of the material which is irradiated or to be irradiated are at least partially used, irradiation planning or irradiation plan validation can in general be carried out more precisely, corresponding to the proposed method. Thus in the specific case of tumour irradiation, the effective dose in the tumour can be optimised, and the surrounding healthy tissue can also be optimally preserved.

In a version of the method for determining an effective dose distribution, a microscopic dose distribution is at least partially determined from the fluence distribution. In this case the microscopic dose distribution, in particular the local dose distribution, can be determined with at least partial use of the radial dose distribution around a single ion trace. The radial dose distribution describes the expected value of the local energy deposition as a function of the distance from the trajectory of the ion trace. The advantage of using the radial dose distribution is that in this way it is possible to refer directly to the effects after photon irradiation. The radial dose distribution can be generated by Monte Carlo simulations, for example. Another possibility exists through analytical dose description of an amorphous path structure.

In a further version of the method, the microscopic, spatial damage distribution (rSv) is at least partially determined from the microscopic dose distribution (mDv), which can be caused by the particle beam or by the induced fluence/energy distribution, the probability, which is required for this purpose, of a local damage induction being at least partially deduced from an associated photon dose effect curve (PEK1). In particular, the spatial damage distribution can be determined by the spatial distribution of the damage events. The photon dose effect curves are known per se, and are usually determined experimentally. For example, the mean number of damage events can often be described by a linear-quadratic relation: $N_{damage}=\gamma D_x+\delta D_x$. $D_x$ here is the X-ray or photon dose, and $\gamma$ and $\delta$ are material-specific constants such as polymerisation events in a monomer crystal of a GafChromic film, or parameters for the yield of double strand breaks.

The action of photon beams is characterised in that the spatial distribution of the occurring damage events is distributed uniformly stochastically on the basis of the physical properties of the energy deposition of photons. If the sensitive volume is divided into partial volumes, which are also called parcels, it can be assumed that each parcel has the same damage density distribution. This means that a uniform damage distribution exists in each parcel.

In contrast, for a sensitive volume which is divided into parcels and irradiated with ions, because of the extremely localised energy deposition of ion beams a heterogeneous damage distribution is present. If the sensitive volume is divided into parcels of a size less than, or less than or equal to, $1\times1\times1$ nm$^3$ ($\leq1\times1\times1$ nm$^3$), and in each parcel the microscopic dose, in particular the local microscopic dose distribution, is determined, a microscopic, spatial damage distribution rSv can thus be determined.

In a further preferred version of the method, the expected value for the number of correlated damage events (AkS) in a suitably chosen partial volume of a sensitive volume is determined more precisely at least partially from the spatial, microscopic damage distribution. In this case the term "correlated damage event" means damage which can occur through the spatial interaction of individual damage events. The spatial correlation can be defined by analysing the distances between the individual damage events. In the case of biological material, for example, a correlated damage event can be defined by the combination of two single strand breaks of the DNA, resulting a DNA double strand break, or two double strand breaks, which result in damage which is difficult for the biological material to repair. The advantage of using correlated damage events is that in this way, in particular, the non-linear reaction of materials or cells to irradiation can be better taken into account.

In a further preferred version of the method for irradiation and of the method for determining the action of the particle beam on a material which is at least partially irradiated or to be irradiated, the material in the irradiation volume is at least partially a biological material. In this case the material can include material built of cells, cell cultures and/or tissue, e.g. tumour tissue. However, the volume can simultaneously also include other material, e.g. a metal implant together with biological tissue.

In a further preferred version of the method, the sensitive volume comprises at least partially at least one sub-volume and/or partial volume of the biological material, in particular a cell. In particular, the sensitive volume comprises a partial volume of a cell. It can preferably be a cell nucleus. Accordingly, the extent of the sensitive volume for determining the local, microscopic dose distribution can correspond to the typical dimensions of a cell, i.e. approximately 10 μm. For subdividing the sensitive volume into the parcels described above, the resolution can be in the nanometer range, i.e. the dimension of one of the parcels described above is of the order of magnitude of typically ≤1 nm. The advantage of observing on the nanometer scale is that with a sufficiently fine resolution, the microscopic dose within a parcel can be assumed to be constant to a first approximation. This assumption makes it possible to deduce the action of energy deposition of ion beams within a parcel from the dose effect curve for photon radiation.

In a further version of the method, a photon dose (PD1) which would have been necessary in order to achieve the same yield of correlated damage events as after ion irradiation, i.e. the same number of correlated damage events (AkS) relative to the total number of individual damage events or of isolated and correlated damage events, is determined. This means that for a macroscopic photon dose within the irradiation field, a spatial distribution of damage events, their type and their number is determined according to the photon dose effect curve PEK1, from which the expected value of the number of correlated damage events can be determined. In particular, the result is thus a photon dose PD1 which results in the same yield of correlated damage events as after ion radiation. For example, for the expected value of the number of double strand break pairs within a specified distance, it can be assumed that it depends quadratically on the macroscopic photon dose. In particular, this makes rapid determination of PD1 possible on the basis of the simulation of the yield of correlated damage events at a specified photon dose. For this purpose, it is assumed that with parcels which are chosen to be sufficiently small and with equal local dose, the same damage is induced with photon and ion irradiation. The reason for this can also be that with a sufficiently small parcel volume, even in the case of ion beams, the expected value of the energy deposition in this volume can be assumed to be homogeneously distributed, and can thus be compared directly with the action of irradiation of photon beams. In this case, it is advantageous that the number of damage events which are known from photon irradiation can be transferred in this dimension to a material irradiated with ions.

In a further version of the method, from a second photon dose effect curve for the observable effect (PEK2), an effect (E1) associated with the photon dose (PD1) is at least partially determined. In contrast to the photon dose effect curve (PEK1), which describes the local, microscopic or molecular damage, the photon dose effect curve (PEK2) represents the macroscopically observable effect. For example, in the case of cells, PEK2 can describe the inactivation of cells, e.g. characterised by the linear-quadratic parameters $\alpha_x$ and $\beta_x$, which are known for many cell and tissue types. In the case of tissues or organs, PEK2 can describe the probability of tissue damage or organ failure. Similarly to PEK1, there is an advantage in that by reference to the experimental photon data, with PEK2 high precision of the determined biological effects for ion irradiation can be achieved. Additionally, with this method, compared with other methods, the computation times can be drastically reduced.

In a further preferred version of the method, the observable effect (E2) for the given fluence distribution is at least partially determined from the scaling of the biologically relevant effect (E1) corresponding to the ratio of the photon dose (PD1) and the ion dose (ID) deposited in the sensitive volume corresponding to the fluence distribution. In particular, the observable effect (E2) can be calculated as follows:

$$E2 = E1 \cdot \frac{ID}{PD1} \text{ or } E2 = E1 \cdot \frac{AkS_2}{AkS_1} \tag{6}$$

where it can be assumed, for example, that E2 is produced by a single ion with associated dose deposition ID and associated PD1. Alternatively and preferably, it can be assumed that E2 is produced by a single ion, and AkS1 and AkS2 describe the number of correlated damage events by the photon dose PD1 and ion dose ID respectively.

Alternatively, the action of the particle beam can also be determined directly from the number of isolated and correlated damage events, if the effect of these damage types can be deduced from the photon dose effect curve:

$$E2 = AiS2 \cdot \varepsilon_i + AkS2 \cdot \varepsilon_k \tag{7}$$

AiS2 here denotes the number of isolated damage events, and AKS2 denotes the number of correlated damage events which can be induced by one ion; $\varepsilon_i$ and $\varepsilon_k$ describe the action of individual isolated and correlated damage events respectively.

In a further version of the method, the effective dose is at least partially determined from the photon dose (PD2) associated with the observable effect (E2). Thus by suitable optimisation methods, the ion dose for each point of the irradiation field can be chosen so that in this way a specified effect can be achieved at every point of the irradiation volume. In the case of a mixed beam field, for example, PD2 can also be determined by observing the beam field at every point of the irradiation field according to the methods which are known in the prior art. In this case, in particular, the so-called intrinsic RBW of individual ions can be used, it being possible to determine the intrinsic RBW as follows:

$$RBW_{int} = \frac{\alpha_{int}}{\alpha_X} = \frac{E2_{single}}{ID_{single} \cdot \alpha_X} \tag{8}$$

where $\alpha_{int} * ID_{single}$ corresponds to the biological effect $E2_{single}$ of a single ion with dose deposition $ID_{single}$.

According to the publication Kramer and Scholz, Physics in Medicine and Biology, Vol. 51, pp. 1959-1970, 2006, $\beta_{int}$ can be obtained from $\alpha_{int}$, and from $\alpha_{int}$ and $\beta_{int}$ finally the effect E2 for the whole mixed beam field which is generated according to the fluence distribution can be obtained. The effect after ion irradiation can be described, for example, by means of the linear-quadratic parameters $\alpha_{ion}$ and $\beta_{ion}$.

An advantage of the method can be seen in that it allows direct transfer of experience with conventional irradiation to irradiation with particle beams. A further advantage of the proposed method is that the $RBW_{int}$ values can be calculated in advance for individual ions from protons to neon and for energies from 0.1 MeV/u to 1 GeV/u, independently of the existing beam field, and stored in the form of tables, before E2 is calculated for the mixed beam field. This can result in a further considerable saving of computation time.

An embodiment of the invention provides a method for irradiating a target volume with a particle beam, having the following steps:—determining a fluence and/or energy distribution within the irradiation volume (46) which includes the target volume (44); —determining an effective dose distribution resulting from the fluence and/or energy distribution, the action of the particle beam on the material of the irradiation volume (46) being used, which action is based at least partially on the microscopic damage correlation according to a method for determining the action of a particle beam in a material.

The properties, features and advantages of the method for irradiation planning apply similarly to the method for irradiating a target volume.

An embodiment of the invention provides an irradiation plan for irradiating an irradiation volume, which comprises a target volume, it being possible to compile the irradiation plan, and/or the irradiation plan having been compiled, at least partially using the method described above. Consequently, for producing the irradiation plan, data which the effective dose distribution resulting from a fluence distribution determines are used, the relevant, observable effect on the material of the irradiation volume being determined at least partially on the basis of the macroscopic damage correlation, and also in particular on the basis of the number of correlated damage events (AkS).

An embodiment of the invention provides a beam modification facility, which can be produced and/or operated using the method described above for irradiating a target volume. The beam modification facility can have an active and/or passive device which is set up to carry out the method. An active beam modification facility can be, for example, a raster scan facility, which guides the particle beam over the target volume according to a location and energy parameter field. A passive beam modification facility can be, for example, a filter element, which was designed or produced by means of the proposed method. The filter element which was designed in this way can then be built into an irradiation facility. In this case, by means of the filter element, an energy and thus the penetration depth (z direction) of the ion or particle beam can be modified, while the x and y directions are each shut down by deflecting the beam by means of a scanner. Thus by interaction of the passive filter element and the active scanner, the target volume to be irradiated can be scanned.

An embodiment of the invention provides an irradiation device, which has at least one beam modification facility, which includes the features described above. In this case the irradiation device can include, in particular, an accelerator device to generate and accelerate a particle beam, and have a beam modification facility, by means of which a target volume to be irradiated can be detected in all three spatial directions. In this case the beam modification device can have both passive and active facilities and a combination of passive and active facilities for changing the beam energy and beam position and/or beam axis at the location of the target volume. The irradiation device preferably has a control system to control the accelerator device, and at least one beam modification facility for irradiating objects, in particular patients. In this way, the irradiation device can be controlled by means of the control system, the control system having a facility in which an irradiation plan is stored or by means of which a corresponding irradiation plan can be generated.

FIG. 1 shows, in schematic representation, a beam modification facility 10 and its action on a monoenergetic ion or particle beam 12. The monoenergetic ion beam 12 is shown schematically using arrows 14 of equal length. The arrows 16a to 16i represent ion beams of different energies, and thus an ion beam 16 which is not monoenergetic, i.e. has ions of different energies. In the lower part of FIG. 1, a diagram is shown in schematic representation. It shows a Bragg peak 18' (shown at left), 24 (shown at right) in a material to be irradiated. The Bragg peak 18' shows the relative dose as a function of the penetration depth in the material. The relative dose is plotted on an axis 20 called the y axis, and the penetration depth is plotted on an axis 22 called the x axis. The course of the curve of the Bragg peak 18 describes the course of the dose as a function of the depth for irradiation with monoenergetic ions. The Bragg peak 24 describes the relative dose in the material as a function of the penetration depth for an ion beam 16 with the different energies shown by the arrows 16a to 16i. The Bragg peak 24 is called the extended Bragg peak 24, and consists of a superimposition of individual Bragg peaks 19a to 19i, each for an energy of the ion beam 16, shown symbolically by the arrows 16a to 16i. The ion beam 16 can be generated from the ion beam 12 by means of the beam modification facility 10. The relative dose corresponds here to a deposited dose in an irradiation volume. The zero point 26 of the x axis 22 corresponds to the surface of the irradiation volume.

In this case, the action of the beam modification facility 10, using which a target volume can be irradiated with a specified dose distribution, is shown schematically. For this purpose, a monoenergetic beam is modulated with respect to beam energy and penetration depth by active or passive beam guidance elements of the beam modification facility 10, so that the desired dose can be applied to a specified depth range. The arrow 28 symbolises the action of the beam modification facility 10, from the Bragg peak 18 for monoenergetic ion irradiation to the Bragg peak 24 for the ion beam 16.

Figure 2:
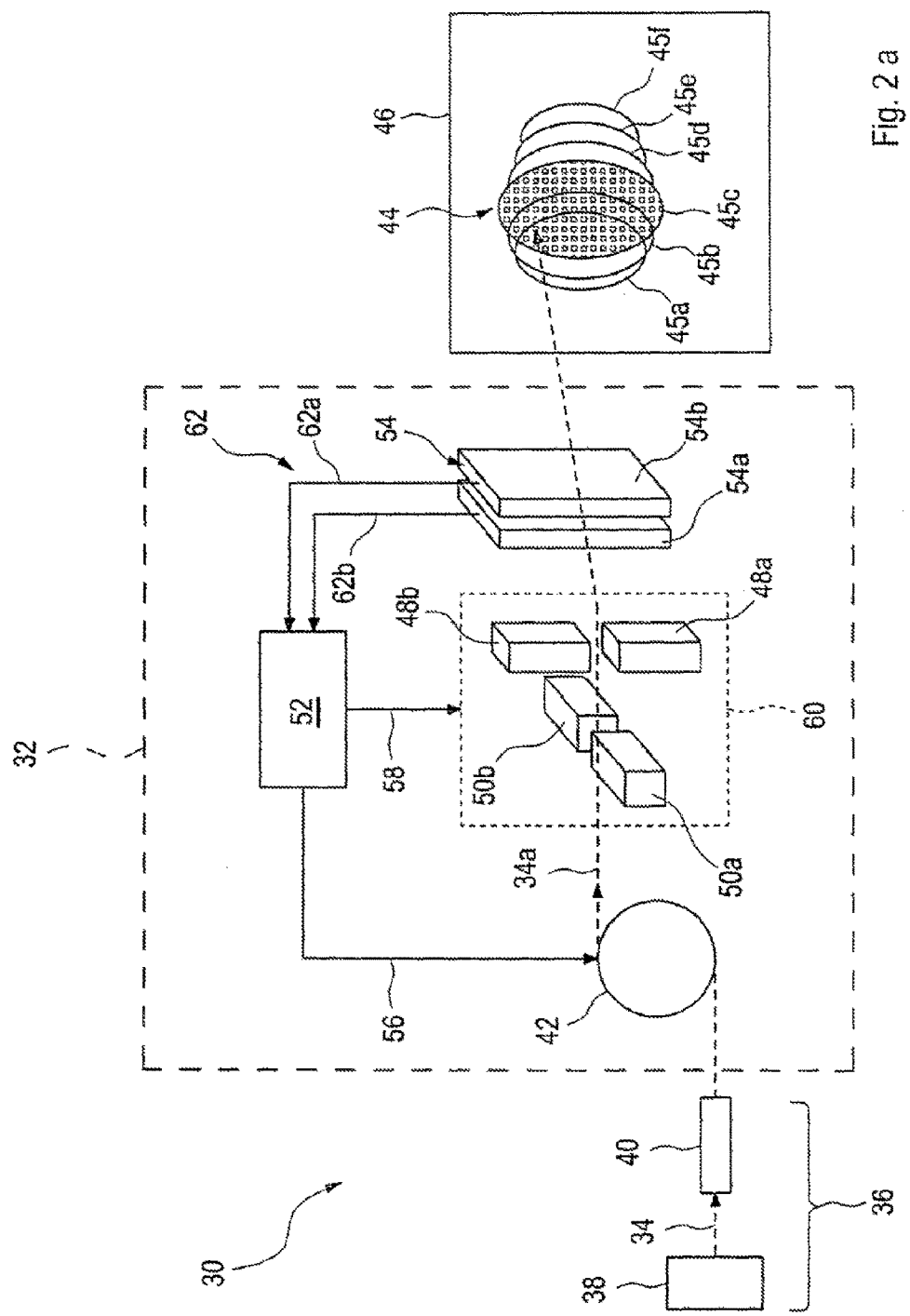
FIGS. 2a and 2b are schematic representations of an irradiation device with an active beam modification facility (FIG. 2a) and with a passive beam modification facility (FIG. 2b)

FIG. 2 shows different possibilities for implementing the beam modification facility 10. FIG. 2a shows, in schematic representation, a structure of an accelerator facility 36 which is set up as an acceleration device or particle therapy system 30, with an active beam modification facility 32, which includes active beam guidance and beam application. The particle therapy system 30 typically has a beam generation facility 38 which generates a particle beam 34, and a beam acceleration facility 40. The beam generation facility 38 typically has a particle source, e.g. an ion source. The beam acceleration facility typically has a low energy accelerator unit and associated beam guidance. Connected downstream from the accelerator facility 36 are a synchrotron 42, a cyclotron or another accelerator, and a high energy beam transport facility. After the synchrotron 42, a particle beam 34a with the necessary energy for irradiation is provided. Particles such as protons, pions, helium ions, carbon ions, oxygen ions or other charged particles or particles of chemical elements or compounds called ions are typically used as particles. The terms ions and particles are therefore used synonymously in the invention.

In FIG. 2, as an example, the ion source 38, a linear accelerator 40 and a synchrotron 42 are shown. The accelerator facility 36 and the high energy acceleration facility which is connected downstream therefrom can also have any other accelerator which is capable of providing a particle beam 34a, in particular of charged ions, with the necessary energy for irradiation of a target volume 44. For use in tumour therapy, typically accelerator facilities 36 which provide an ion beam 34a with a maximum energy of the particles of the order of magnitude of typically 1 GeV/amu are used.

The target volume 44 is arranged in an entity or irradiation volume 46. The entity 46 can include the volume surrounding the target volume 44 and/or the whole object to be irradiated. The target volume 44 to be irradiated can be a volume in any form which is to be exposed to the particle radiation, e.g. a film detector system, a volume filled with cell culture samples or a tumour volume in a patient (not shown). The target volume 44 can be both a target volume 44 at rest and a moving target volume 44. The target volume 44 is typically divided into slices 45a, 45b, 45c, 45d, 45e, 45f, which are each irradiated by an ion beam 34a with a specific energy which is necessary for the respective slice 45a, 45b, 45c, 45d, 45e, 45f. The energy in each case is usually set by the synchrotron 42, and is variable.

In order to apply the total dose in the target volume 44 to be irradiated, the target volume 44 is irradiated by a raster scan method, for example. In this case a thin pencil beam is steered, using deflection magnets 48a, 48b, 50a and 50b, laterally over the volume 46 to be irradiated, the beam energy and thus the penetration depth of the beam 34a is varied by varying the high energy accelerator setting or the absorber thickness, and the beam is thus guided in the longitudinal direction over the volume to be irradiated, in particular over the slices 45a, 45b, 45c, 45d, 45e, 45f.

For this purpose, the irradiation device 30 has a flow control facility 52 and at least one detector 54 to monitor the parameters of the ion beam 34a, called the ion beam parameters. The flow control facility 52 is coupled via a typically electrical connection 56 to the accelerator facility 36, in particular the synchrotron 42, and via a connection 58 to a raster scan facility 60. The flow controller 52 is connected to the detector 54 via a connection 62. Thus values (parameters of the particle beam 34a) which are determined via the detector 54, e.g. the energy and position of the particle beam 34a, can be used to control and regulate the irradiation device 36, in particular the synchrotron 42. The detector 54 can be constructed of a plurality of detector units. In the shown embodiment, the detector 54 is made up of two detector units 54a and 54b, and consequently the connection 62 comprises two connections 62a and 62b. An example of a detector 54 for determining the ion beam parameters is, for example, an ionisation chamber 54a and a multiwire proportional chamber 54b, which can be used or are suitable as beam intensity or beam position monitors.

The flow control facility 52 represents the control system of the particle beam system 30, and thus controls the individual components of the system 30, e.g. the accelerator facility 36, the synchrotron 42 and the magnets 48a, 48b, 50a and 50b of the raster scan facility 60. Additionally, measurement data such as data of the detector 54 can be read into and/or stored in the flow control facility 52 for monitoring the beam parameters.

Usually, the beam parameters of the particle beam system 30 are controlled using an irradiation plan, which is generated before irradiation. This irradiation plan is typically produced in a planning facility before the start of irradiation of the target volume 44. However, it can also be provided that the irradiation plan is produced and/or modified when the irradiation has already begun. Such irradiation plans can be produced by a method 200 (shown in FIG. 4).

The beam modification facility shown in FIG. 2a is an active beam modification facility 32. The arrangements of the components of the particle beam system 30 shown in FIG. 2a are merely exemplary. Other arrangements, in particular other components for beam generation and beam modification, can be used.

FIG. 2b shows, in schematic representation, an example of another embodiment of an irradiation facility 66. In this case, the beam energy (energy of the ion beam) is modulated via a so-called ridge filter system 68. The shape of this filter 68 is designed so that by variable thickness at various points of the filter, an ion beam 34a is reduced to different extents. Thus by the design of the filter 68, the precise form of the depth dose distribution of the ion beam in the target volume 44 is uniquely fixed. In reverse, a specified depth dose distribution determines the design of the associated filter 68. The technical design of the filter 68 thus typically depends on the determined irradiation plan in each case. The method 200 for producing an irradiation plan can be used in the production of the filter system 68 and/or individual components, and can thus be used, for example, to generate control data for CNC production machines. The data that are generated by the proposed method for the effective dose distribution to be achieved can thus be used in production of the filter 68. The beam modification facility 10 shown in FIG. 2b is designated as a passive beam modification facility 70. The passive beam modification facility 70 typically includes, as well as the filter 68, a collimator facility 71, of which only one collimator is shown schematically.

In addition to the active and passive methods for beam modification described above, mixed methods for implementing a beam modification facility are also conceivable.

FIG. 3 shows schematically the expected value of the energy deposition on a micrometer scale for photon beams (3d) and ion beams (3b). The changed action of ion beams compared with photon radiation is caused by the different microscopic distribution of the energy deposition 72 of the different beam types, that is ion radiation and photon radiation. In the case of photon radiation, this distribution on average takes place evenly over a surface 74 under observation. In contrast, ions deposit their energy very heterogeneously distributed. Near a trajectory or trace 76 of an ion (at a distance of a few nm), extremely high doses D (up to about $10^6$ Gy) can be deposited, whereas at greater distances (a few μm) from the trajectory 76, the dose values can fall very quickly to very low values (<<1 Gy). The overall result is a very heterogeneous distribution 78 (3b) of the deposited energy. However, if only a small partial region ($nm^3$) 80 (3c) of this heterogeneous distribution 78 is considered, the dose which is deposited in this partial region can again be assumed to be approximately constant. This distribution thus resembles the distribution which would be expected for irradiation with photons at the same local dose.

Thus by selecting a suitable partial region 80 on the basis of the similarity described above, the action of ion beams in a small partial region can be deduced from the action of photon radiation. In particular, as the partial region, in particular as the partial volume, a sensitive volume is chosen.

The exploitation of this principle to calculate the action of ion beams in order to determine and optimise an irradiation plan is explained in more detail below on the basis of the method shown in FIG. 4.

FIG. 4 shows a flowchart of a method 200 for producing an irradiation plan which is used to irradiate the target volume 44 with the particle beam 34a (see FIG. 2). In determining the irradiation plan, the calculation begins in method step 210. In method step 220, a fluence distribution in a target volume 44 of the irradiation volume 46 is determined. The target volume 44 can comprise an inorganic, organic or biological material to be irradiated. Biological material typically consists of cells. The target volume 44 can, for example, comprise at least one cell culture and/or at least one tissue, e.g. a tumour tissue.

In method step 230, an effective dose distribution resulting from the fluence distribution is determined, data which determine the observable effect in the respective material on the basis of a microscopic, in particular local, damage correlation being used. In step 235, there is a query whether the desired target dose for the given fluence distribution is reached. If so, the method is ended in step 240. If not, the fluence distribution is modified corresponding to the difference between the setpoint value and the actual value of the effective dose distribution, and processing then continues with step 220.

The method 200 can be used to irradiate the target volume 44, to create an irradiation plan which is used to irradiate the target volume 44, and/or to validate the irradiation plan before or after the target volume 44 has been irradiated.

The method 200 includes, in method step 230, the use of a biophysical model, since the use of particle beams in irradiation of material, in particular of biological tissue in tumour therapy, requires precise knowledge of the biological actions of the particle beams. The biophysical model which is used is called the local effect model (LEM), and takes into account the complex dependency of the effectiveness of parameters of the particle beam 34a, such as type of particles (ion type), ion beam energy, ion dose and material, in particular cell or tissue type. In this case, in calculating the effective dose distribution, the biological action of the local energy deposition within a cell or cell nucleus is taken into account.

FIG. 5 shows a flowchart of the method steps which can be included in method step 230 of the flowchart of FIG. 4.

In method step 250, a microscopic dose distribution mDv is determined from the fluence distribution. The microscopic dose distribution, in particular the local dose distribution, can be determined with at least partial use of the radial dose distribution around a single ion trace. The radial dose distribution describes the expected value of the local energy deposition as a function of the distance from the trajectory of the ion trace. The advantage of using the radial dose distribution is that in this way it is possible to refer directly to the effects after photon irradiation. The radial dose distribution can be generated by Monte Carlo simulations, for example. Another possibility exists through analytical dose description of an amorphous path structure. The radial dose distribution describes the expected value of the local energy deposition as a function of the distance from the trajectory of the ion trace. The advantage of using the radial dose distribution is that in this way it is possible to refer directly to the effects after photon irradiation. The radial dose distribution can be generated by Monte Carlo simulations, for example. Another possibility exists through analytical dose description of an amorphous path structure. In the form as they are used in the LEM models which are known in the prior art:

$$D_{track}(r) = \begin{cases} \lambda LET/r_{min}^2: r < r_{min} \\ \lambda LET/r^2: r_{min} \leq r \leq r_{max} \\ 0: r > r_{max} \end{cases} \quad (9)$$

where $\lambda$ is a normalisation constant, LET describes the linear energy transfer, $r_{min}$ characterises the inner region with constant dose, and $r_{max}$ is the maximum trace radius, e.g. determined by:

$$r_{max} = \gamma E^\delta \quad (10)$$

where $\gamma=0.062$, $\delta=1.7$. $r_{max}$ is given in μm, and E is the specific energy of the ion in MeV/u. LET denotes the energy per length unit of distance which is deposited by an ion when it passes through water-equivalent material, and is given in keV/μm.

In method step 260, a spatial damage distribution rSv is at least partially determined from the microscopic dose distribution mDv, the probability of a local damage induction being at least partially deduced from an associated photon dose effect curve PEK1. In the case of a biological target volume, e.g. cells or tissue, the spatial damage distribution rSv can be given by the distribution of double strand breaks (DSB) in the cell nucleus, for example. In this case, the associated photon dose effect curve PEK1 is the dose effect curve which describes the induction of double strand breaks as a function of the dose.

In method step 270, the expected value for the number of correlated damage events in a suitably chosen volume is at least partially determined from the spatial damage distribution rSv within a sensitive volume. In the case of biological material, the sensitive volume comprises at least one sub-volume and/or partial volume of a cell of the biological material. As described above, the advantage of the division into a sub-volume and/or partial volume is that in a partial region, the distribution of the expected value of the energy deposition is almost uniform even in the case of ion beams, and is thus similar to the distribution in the case of photon beams.

The biological effect in these small volumes should therefore correspond to that which is expected for photon radiation with a dose of equal size. This makes it possible to deduce the biological action of ion beams from that of photon beams.

In method step 280, a photon dose PD1 which would have been required to achieve the same yield of correlated damage events is determined. The correlated damage events are typically combinations of double strand breaks which are induced within a specified distance. However, combinations of double strand breaks with single strand breaks or other DNA deterioration which is relevant to cell functions can also be considered as correlated damage events.

In method step 290, an effect E1 associated with the photon dose PD1 is determined from a second photon dose effect curve PEK2 for the observable effect. In the case of irradiation of tumour tissue, the observable effect can be destruction of the tumour, for example. However, the observable effect can also concern the surrounding healthy normal tissue; for example, it can be deterioration of the skin in front of the tumour in the entry channel of the irradiation field. In these cases, the photon dose effect curve PEK2 would represent dependency of the tumour destruction and skin deterioration as a function of the irradiation dose.

In method step 300, an observable effect E2 for the given fluence distribution is determined by scaling the observable effect E1 corresponding to the ratio of the photon dose PD1 and the ion dose deposited in the sensitive volume corresponding to the fluence distribution.

Preferably, in method step 300 an observable effect E2 for the given fluence distribution is determined by scaling the observable effect E1 corresponding to the ratio of the number of correlated damage events after ion irradiation ($AkS_2$) to the number of correlated damage events after photon irradiation ($AkS_1$).

In method step 310, the effective dose is determined as the photon dose PD2 which would result in the same effect E2 as the ion dose ID. The relative biological effectiveness is then given by the ratio of the photon dose PD2 to the ion dose ID.

With the method 200, predictions about observable effects, e.g. the probability of survival of cells in an irradiated cell culture, the probability of tumour destruction or the probability of normal tissue deterioration after irradiation with a particle beam 34a can be made.

Typically, with the method 200 the action over the whole energy range which is relevant for use in tumour therapy and also over a wide range of different ion types is described correctly. Example calculations which are carried out by the method 200 are shown and described in the following figures.

The calculations can be based on the following descriptions and parameters, which are not obligatory for the proposed determination of the effective dose distribution:

1) The cell nucleus, as a sensitive volume, is simulated as a cylinder with a volume of 500 μm³. The radius of the cell nucleus is determined using experimental data. The height of the cell nucleus is given accordingly.

2) The radial dose distribution around individual ion traces is given according to equation (11). Here, $r_{min}$=v/c*6.5 nm is energy-dependent, where v is the ion speed and c is the speed of light.

3) From experimental data, PEK1 becomes $N_{DSB}=\gamma_{DSB}*D_\gamma$, where $\gamma_{DSB}$=30 DSBs/Gy/cell and $D_\gamma$ is the photon dose. Additionally, a further cluster effect of single strand breaks (ESB), as in Elsässer and Scholz 2007, Radiation Research, Vol. 167, 319-329, is taken into account.

4) PEK2 is given by:

$$S(D) = \begin{cases} e^{-\alpha D-\beta D^2}; & D \leq D_t \\ S_t e^{-s \cdot [\eta(D)D-D_t]}; & D > D_t \end{cases} \quad (11)$$

where α, β are the linear-quadratic parameters which are usually given by "in vitro" measurements or clinical data. s=α+2β$D_t$ is the gradient above a threshold value $D_t$, above which, according to experimental knowledge, PEK2 goes into a purely exponential course. $S_t$ is the gradient for D>Dt, and η quantifies the cluster effect of ESB (see above and Elsässer and Scholz 2007, Radiation Research, Vol. 167, 319-329).

5) Correlated damage events are viewed in the example calculations as DSB pairs with a distance less than 440 nm. This value was optimised on the basis of experimental data and applying the method according to the invention. It is independent of ion type, ion energy, dose or biological material.

Figure 6:
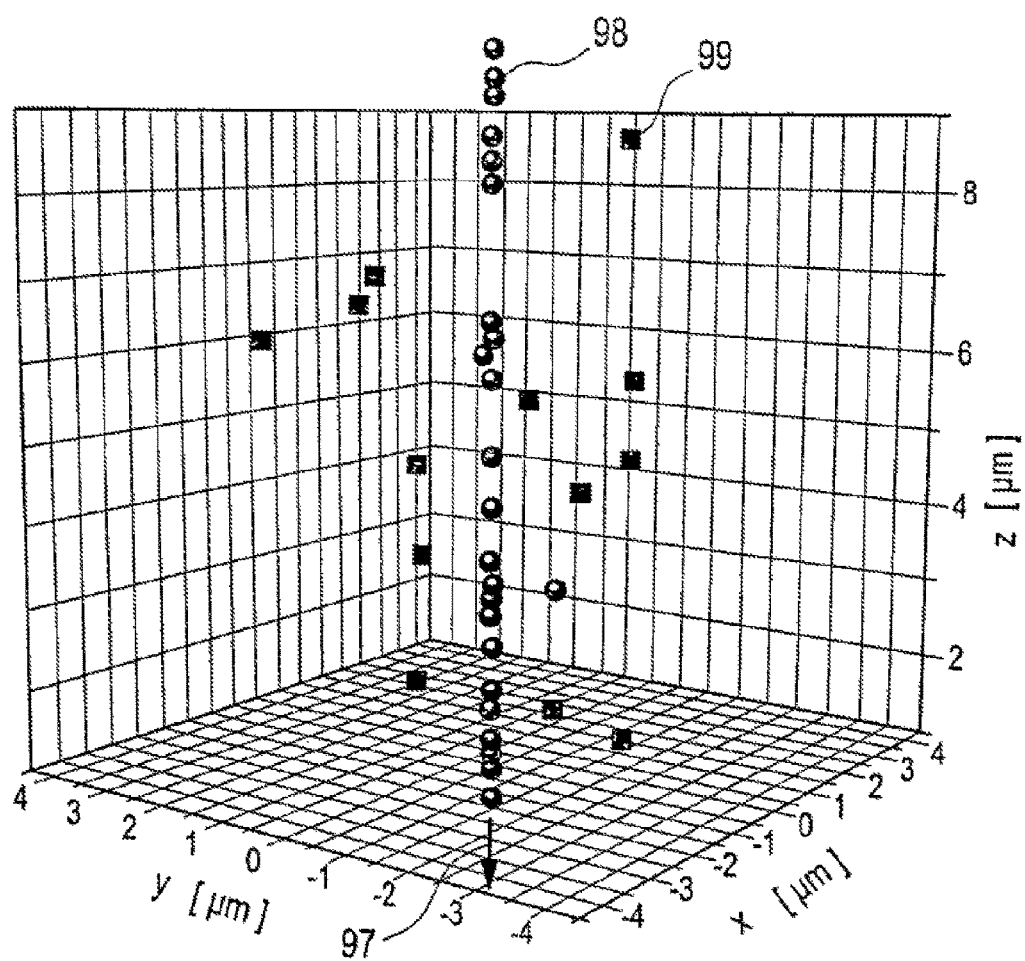
FIG. 6 shows a distribution of DNA damage events in a sensitive volume after irradiation with ions and photons.

FIG. 6 shows a calculated distribution of double strand breaks after irradiation of a cell nucleus with a radius of 5 μm with an ion (11 MeV/u, 153.5 keV/μm) or photons. For both beam types, this was based on the same total energy deposition $D_1$=0.3 Gy, corresponding to the dose deposition of the single ion in the cell nucleus. The three axes x, y, z represent a length extent of the cell nucleus in the x, y and z directions respectively, and the stated numbers correspond to a length in micrometers. The circular symbols 98 each represent a double strand break after an ion has traversed the cell nucleus, whereas the square symbols 99 each represent a double strand break after irradiation with photons. The flight path or trajectory of the ion as such is marked by the arrow 97. It can clearly be seen that the double strand breaks after ion irradiation are located in a narrow region around the ion path. In contrast, the double strand breaks after photon irradiation, which are marked with the symbol 99, are stochastic and approximately uniform within the whole cell nucleus volume.

Because of the different spatial distribution, it is significantly more probable for ion beams to induce correlated damage events, e.g. two double strand breaks, within a specified distance of for example 440 nm.

The ratio of the number of correlated damage events. e.g. double strand break pairs (DSB pairs) to the total number of induced individual damage events or preferably of isolated and correlated damage events, can be considered as a measure for the probability of induction, or alternatively of the yield of correlated damage events. To induce, with photon beams, a similar ratio of the number of correlated damage events AkS to the total number of individual damage events or of isolated and correlated damage events as with ion beams, a significantly higher dose is necessary.

Figure 7:
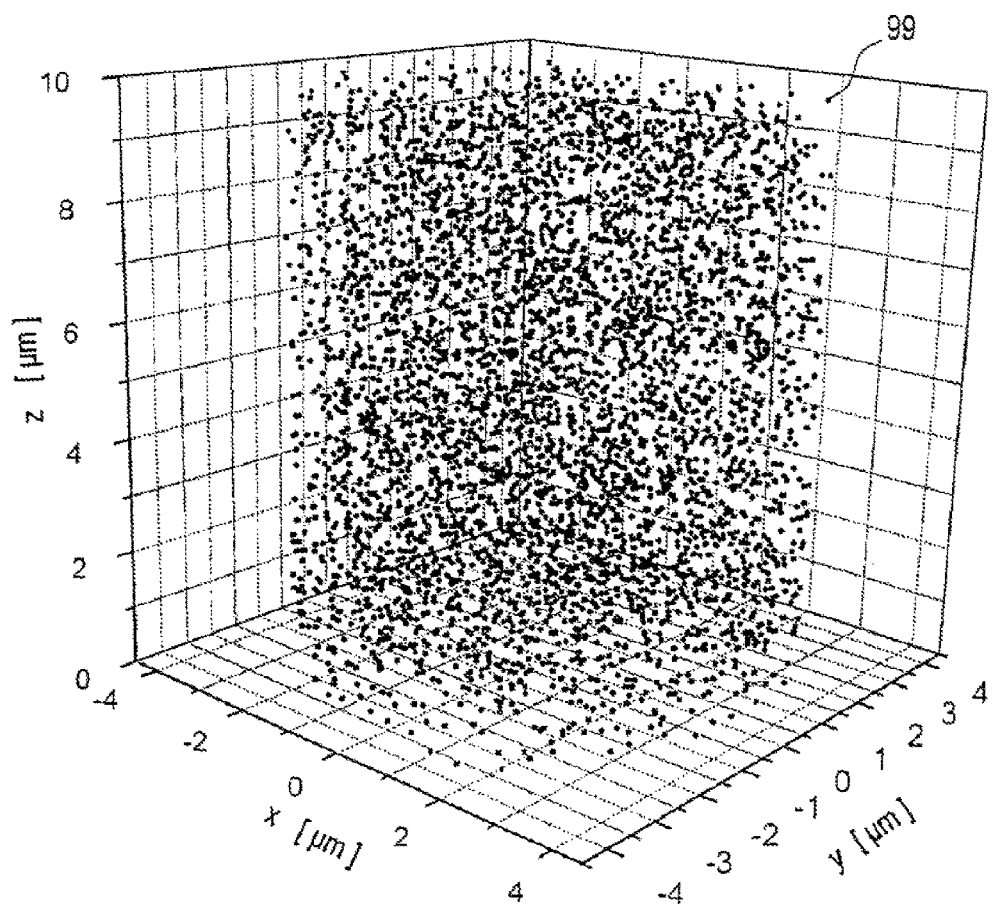
FIG. 7 shows a distribution of DNA damage events in a sensitive volume after photon irradiation, which results in the same yield of correlated damage events as the irradiation with ions shown in FIG. 6.

FIG. 7 shows the calculated distribution of double strand breaks 99 after photon irradiation at a dose which results in the same ratio of correlated damage events to total damage events as the distribution shown in FIG. 6 for ion beams. For a suitably chosen sub-volume of the cell nucleus, therefore, the distribution shown in FIG. 7 can be seen as representative of the action of an ion beam shown in FIG. 6, and thus the action of an ion beam can be deduced from the action of conventional photon beams. The model based on this method is called the generalised local effect model (GLEM).

Figure 8:
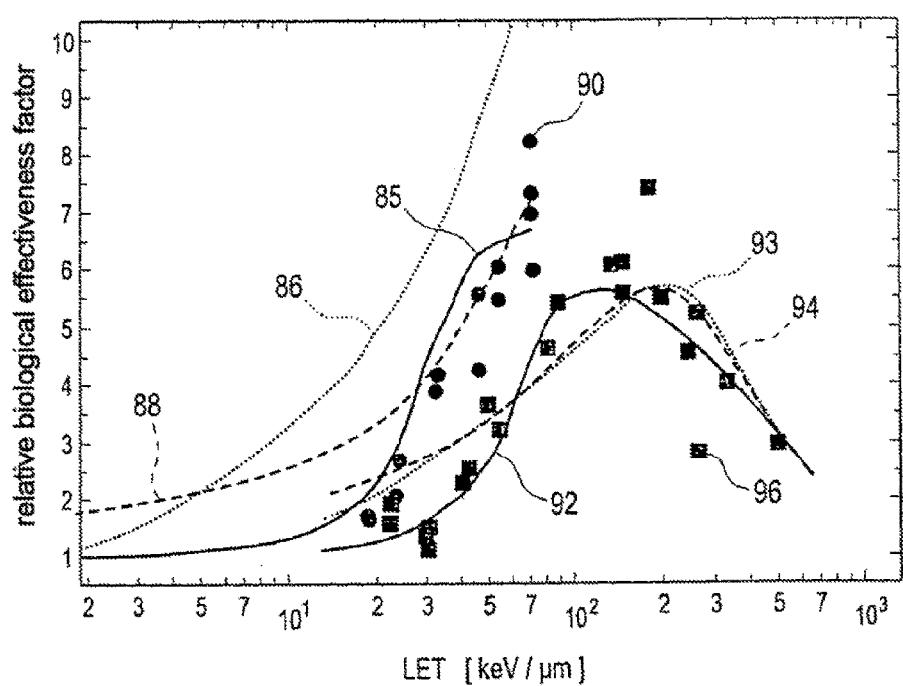
FIG. 8 shows a function of an RBW factor depending on the linear energy transfer (LET)

FIG. 8 shows a calculation, which is carried out using GLEM, of the relative biological effectiveness for the inactivation of HSG (human salivary gland) cells after irradiation with helium and carbon ions. The relative biological effectiveness (RBW) is plotted on they axis as a function of the linear energy transfer (LET) on the x axis. The photon data for PEK2 (α=0.313 Gy$^{-1}$, β=0.0616 Gy$^{-2}$), on which the calculation is based, were taken from Furosawa et al. 2000, Radiation Research, Vol. 154, pp. 485-496. $D_t$=18 Gy and the radius of the cell nucleus is 5 μm.

The curves 85 and 92 denote a functional relation, which is calculated according to the GLEM method, between the maximum RBW factor $RBW_\alpha=\alpha_{ion}/\alpha_x$ and the LET for irradiation with helium and carbon ions, and a comparison with experimental data 90 and 96 (experimental data taken from Furosawa et al. 2000, Radiation Research, Vol. 154, pp. 485-496). Curve 85, 88 and 86 are curves for helium ions, and curve 85 is calculated according to GLEM, curve 86 according to LEM III, and curve 88 according to LEM II. The measurement data which are denoted by round symbols and representatively by 90 are those which were determined after irradiation of a target volume 44 with helium ions. Similarly, curve 92 shows a calculation with GLEM, curve 93 with LEM III, and curve 94 shows a calculation with LEM II, for carbon ions; and the square symbols, symbolised representatively by 96, show the associated experimental values. It can clearly be seen that the curves 85 and 92 best reflect the experimental values. In particular, for a low LET, it can clearly be seen that the curves calculated with GLEM predict the position of the measured values 90 and 96 better.

Figure 9:
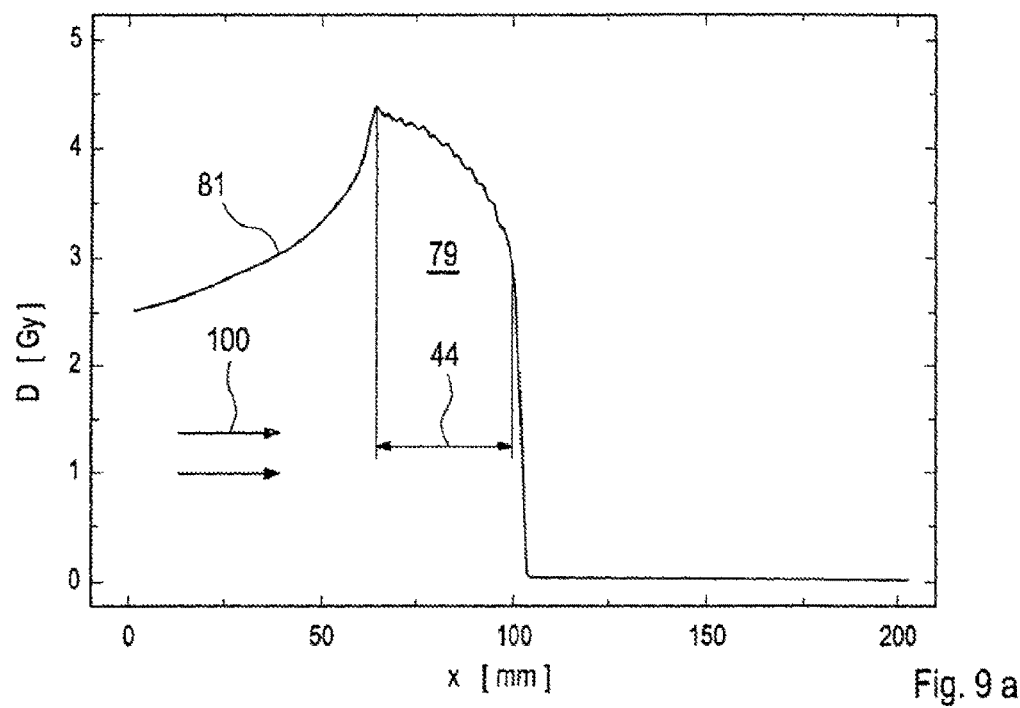
Figure 9:
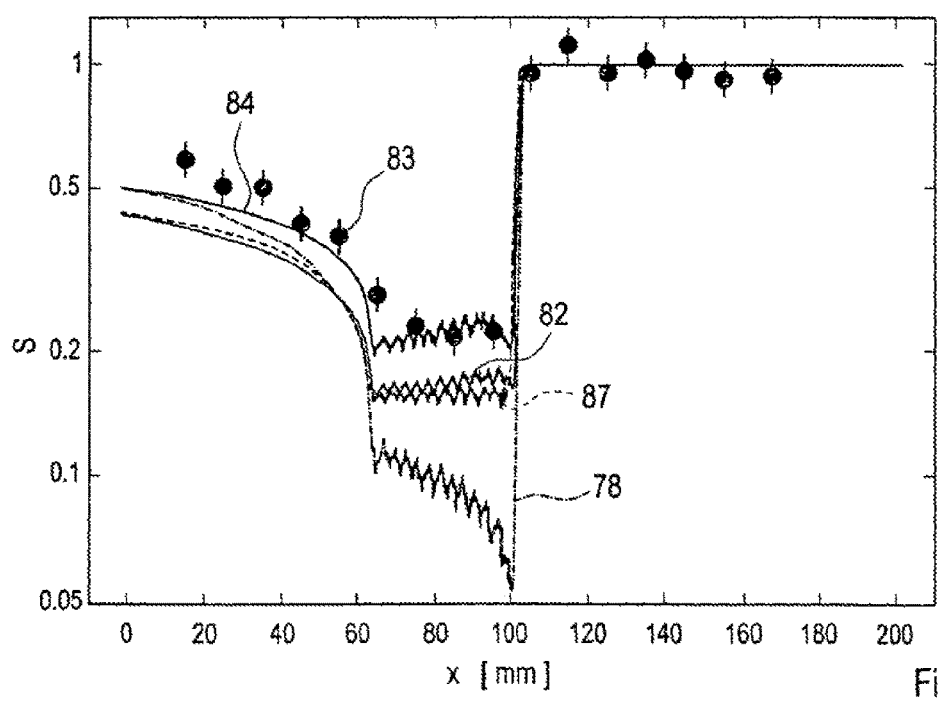

This is confirmed by the comparison shown in FIG. 9. FIG. 9a shows a physical dose profile 81 for a target volume 44 which is irradiated with energy-modulated helium ions (4 cm extended Bragg peak in a water-equivalent depth of 8 cm), depending on the penetration depth x in mm. The reference symbol 79 denotes the dose D which is deposited in the target volume 44. The arrows 100 denote the ion beam. As a comparison with experimental data, the experimentally determined survival of CHO cells, with the parameters of PEK2 $\alpha=0.228$ Gy$^{-1}$, $\beta=0.02$ Gy$^{-2}$ and $D_t=35$ Gy (cell nucleus radius 5 µm), is compared with the calculated survival.

In FIG. 9b, curve 87 represents a result of calculation according to LEM I, curve 82 according to the calculation with LEM II, curve 78 according to the calculation with LEM III, and curve 84 according to the calculation according to GLEM. The filled circles, representatively marked by 83, represent the experimental results (publication by Müller, GSI Report 2004). Here too, the calculation with GLEM shows significantly better agreement with the experimental data compared with the LEM I to LEM III models.

Figure 10:
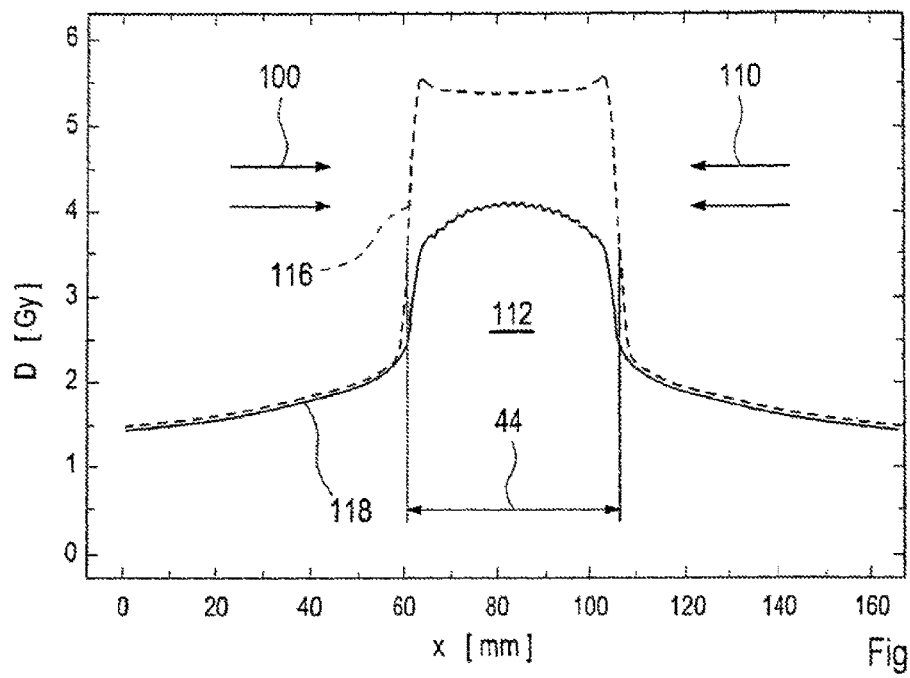
Figure 10:
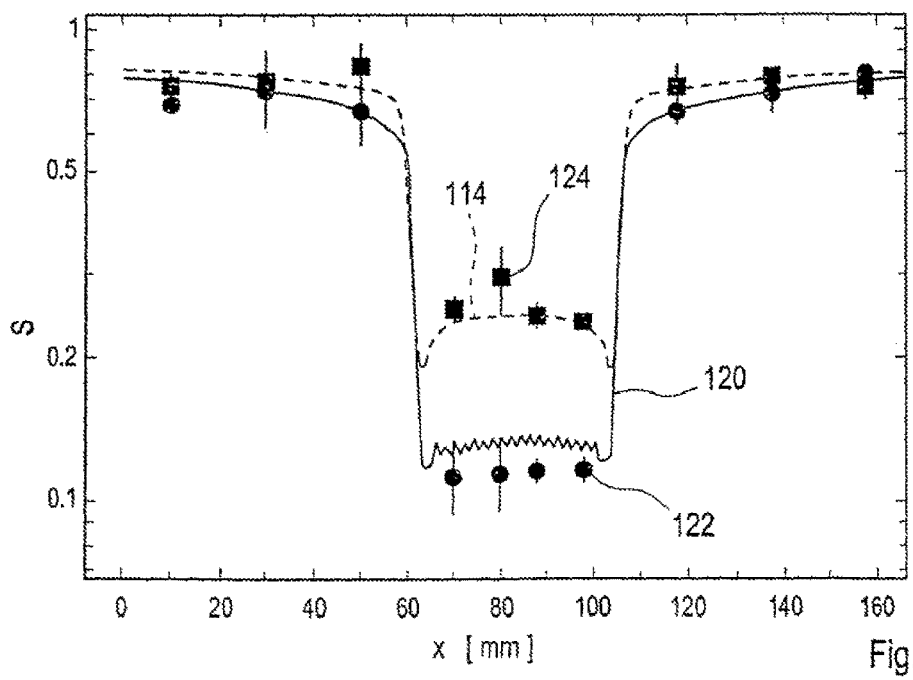

In a further comparison, FIG. 10 shows the calculation of the action of proton and carbon beams in a therapy-like irradiation field, together with the corresponding experimental data for CHO cells with the likewise experimentally determined PEK2 parameters $\alpha=0.105$ Gy$^{-1}$, $\beta=0.025$ Gy$^{-2}$ and $D_t=40$ Gy (cell nucleus radius 6 µm).

FIG. 10a shows the physical dose distribution with two opposing fields, which were irradiated at an angle of 180°. The target volume 44 is irradiated with the particle beam 34a from a first direction, shown schematically by the arrows 100, and a second direction, shown schematically by the arrows 110. Curve 116 shows a physical dose profile D of the carbon irradiation, and curve 118 shows a physical dose profile D of the proton irradiation. The dose is denoted by D, and plotted on the y axis, and the length unit x is plotted on the x axis. The position of the target volume 44 is shown schematically by the region 112.

FIG. 10b shows the calculated and experimentally determined survival of the CHO cells. The square symbols 124 are the measured survival, and the curve 114 is the calculated survival after proton irradiation. The round symbols 122 represent the measured survival, and the curve 120 represents the calculated survival after carbon irradiation. From the comparison of the curve 114 with the measured results 124 for proton radiation which has taken place, and the comparison of the curve 120 with the measured data 122, it can be seen that the effective dose distribution, which was calculated using the GLEM model with the proposed method 200, reproduces the experimental data very well.

The comparisons in FIGS. 8 to 10 thus show that the calculations using the GLEM model according to the invention are most reliably suitable for predicting the effective dose distribution, in particular for particle therapy.

The shown method for irradiation and/or irradiation planning includes a method for determining an action of a particle beam 34a in a material which is at least partially irradiated or to be irradiated. In this method, at least from one parameter, which characterises the particle beam 34a, and from at least one property of the material, the action of the particle beam in the material is determined at least partially on the basis of a microscopic damage correlation. The method for irradiation and/or irradiation planning is a method for determining an action of a particle beam 34a in a material which is at least partially irradiated or to be irradiated, and can also include the steps listed below:

- determining the microscopic damage correlation using a spatial microscopic damage distribution;
- determining the spatial microscopic damage distribution at least partially from a microscopic dose distribution, which is generated by the particle beam 34a, the probability of a local damage induction being deduced at least partially from a first photon dose effect curve;
- determining an expected value for a number of correlated damage events in a suitably chosen partial volume of a sensitive volume, at least partially from the spatial microscopic damage distribution;
- determining a photon dose which would have been necessary in order to reach approximately the same yield of correlated damage events corresponding to the expected value for the particle beam of the number of correlated damage events;
- determining an effect associated with the photon dose, or an associated action, at least partially from a second photon dose effect curve;
- storing actions, which are determined in each case for the various parameters of the particle beam and for the various parameters, in a memory unit, the action of the particle beam in the material to be irradiated being determined on the basis of the microscopic damage correlation for various parameters which characterise the particle beam 34a and/or at least one property of the material, in particular various properties of the material.

Thus the action of a particle beam 34a in a material which is at least partially irradiated or to be irradiated can be determined in a separate method, and stored in a storage medium in the form of data sets, tables, value tables, etc. These data sets, tables etc. can be input to a known method, which is different from the above-mentioned method, for irradiation, in particular for irradiation planning, as input data.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

What is claimed is:

1. A method for generating by a computer, a plan parameter set of control parameters for controlling a radiation generating device so as to irradiate a target volume in an irradiation volume with an ion beam, wherein the target volume comprises a biological material, the method comprising:
   a) providing a test parameter set of control parameters for controlling the radiation generating device;
   b) determining a fluence and/or energy distribution of the ion beam within the target volume that corresponds to the test parameter set;
   c) determining an effective biological dose distribution of the ion beam within the target volume that corresponds to the fluence and/or energy distribution of the ion beam by:
      defining at least one sensitive volume within the biological material to be irradiated, determining, from the fluence and/or energy distribution of the ion beam, a microscopic dose distribution of the ion beam within the at least one sensitive volume, determining, for the at least one sensitive volume, from the microscopic dose distribution of the ion beam within the at least one sensitive volume, a spatial microscopic damage distribution of the ion beam in the at least one sensitive volume by using a first photon dose effect curve that describes a number of damage events per dose unit, determining, for the at least one sensitive volume, from the spatial microscopic damage distribution of the ion beam in the at least one sensitive volume, an expected value of a number of correlated damage events in a sub-micrometer range in the at least one sensitive volume, wherein correlated damage events are combinations of individual damage events within a specified distance, and determining, for the at least one sensitive volume, using the expected value of the number of correlated damage events in a sub-micrometer range in the at least one sensitive volume, an effective biological dose of the ion beam in the biological material, and determining, using the effective biological dose of the ion beam in the biological material, the effective biological dose distribution of the ion beam in the target volume;

d) evaluating whether the effective biological dose distribution of the ion beam in the target volume achieves a desired target dose distribution to be deposited within the target volume, and e) if the desired target dose distribution is achieved, storing the test parameter set as the plan parameter set, or otherwise modifying the test parameter set and repeating steps b) through e) using the modified test parameter set.

2. The method of claim 1, wherein determining, using the expected value of the number of correlated damage events in the sub-micrometer range in the at least one sensitive volume, the effective biological dose of the ion beam in the biological material comprises:

determining a yield of correlated damage events of the ion beam, the yield of correlated damage events of the ion beam being an expected value for a number of correlated damage events in a sub-micrometer range relative to a total number of individual damage events in the sub-micrometer range; and determining a first photon dose that would have been required to achieve a yield of correlated damage events equal to the yield of correlated damage events of the ion beam.

3. The method of claim 2, wherein determining, using the expected value of the number of correlated damage events in a sub-micrometer range in at least one sensitive volume, the effective biological dose of the ion beam in the biological material comprises:

determining a first observable effect on the biological material associated with the first photon dose from a second photon dose effect curve.

4. The method of claim 3, wherein the second photon dose effect curve represents a macroscopically observable effect.

5. The method of claim 4, wherein the macroscopically observable effect is the inactivation or the probability of survival of cells.

6. The method of claim 3, wherein determining, using the expected value of the number of correlated damage events in a sub-micrometer range in at least one sensitive volume, the effective biological dose of the ion beam in the biological material further comprises:

determining a second observable effect on the biological material by scaling the first observable effect by a ratio of the first photon dose to a dose deposited in the sensitive volume by the fluence distribution of the ion beam.

7. The method of claim 6, wherein determining, using the expected value of the number of correlated damage events in a sub-micrometer range in at least one sensitive volume, the effective biological dose of the ion beam in the biological material further comprises:

determining a second photon dose that would have been required to achieve the second observable effect on the biological material.

8. The method of claim 7, wherein determining the effective biological dose of the ion beam in the biological material further comprises:

calculating a relative biological effectiveness of the ion beam on the biological material as a ratio of the second photon dose to the dose deposited in the sensitive volume by the fluence and/or energy distribution of the ion beam.

9. The method of claim 1, wherein determining, from the fluence and/or energy distribution of the ion beam, the microscopic dose distribution of the ion beam within at least one sensitive volume at least partially utilizes dose distributions around a-single ion traces, the dose distribution around a single ion trace describing an expected value of a local energy deposition as a function of a distance from the trajectory of the single ion trace.

10. The method of claim 9, wherein the dose distribution around the single ion trace is generated by Monte Carlo simulation.

11. The method of claim 1, wherein the first photon dose effect curve is derived from experimental data.

12. The method of claim 1, wherein the at least one sensitive volumes is divided into a plurality of parcels, wherein determining, from the fluence distribution of the ion beam, the microscopic dose distribution of the ion beam within each of the plurality of parcels includes determining, for each of the plurality of parcels, a microscopic dose, and wherein each respective parcel of the plurality of parcels has a volume such that the distribution of the microscopic dose for the respective parcel is approximately homogeneously distributed therein.

13. The method of claim 12, wherein the volume of each parcel has dimensions on the order of magnitude of 1 nanometer.

14. The method of claim 1, wherein the number of damage events per dose unit described by the first photon dose effect curve is a number of double strand breaks of the DNA in the biological material per dose unit.

15. The method of claim 1, wherein correlated damage events are combinations of two individual double strand breaks of the DNA in the biological material within a specified distance.

16. The method of claim 15, wherein the specified distance is in a range between 100 nanometers and 1 micrometer.

17. The method of claim 1, wherein the biological material comprises at least one cell having a cell nucleus, and wherein the sensitive volume has a volume on the scale of the cell nucleus.

18. The method of claim 3, wherein the second photon dose effect curve is determined experimentally.

19. The method of claim 6, wherein the second observable effect is at least one of a probability of tumor destruction or the probability of normal tissue deterioration.

20. A method for irradiating a target volume in an irradiation volume comprising a biological material according to an irradiation plan including an irradiation plan parameter data set used for controlling, directly or indirectly, an irradiation system for irradiating the target volume in the irradiation volume using an ion beam, wherein the irradiation plan parameter data set accounts for an effect of the ion beam on the biological material, and wherein the effect of the ion beam on the biological material involves the induction of damage events in the biological material, the method comprising:

defining a sensitive volume within the biological material to be irradiated;

determining a fluence distribution of the ion beam;

determining a microscopic dose distribution of the ion beam from the fluence distribution of the ion beam;

determining, from the microscopic dose distribution of the ion beam, a spatial microscopic damage distribution of the ion beam in the sensitive volume which is deduced from a first photon dose effect curve that describes a number of damage events per dose unit;

determining an expected value for a number of correlated damage events in a sub-micrometer range in the sensitive volume from the spatial microscopic damage distribution of the ion beam in the sensitive volume, wherein correlated damage events are combinations of individual damage events within a specified distance;

determining, using the expected value of the number of correlated damage events in a sub-micrometer range in the sensitive volume, the effect of the ion beam on the biological material;

using the data that indicate the effect of the ion beam on the material for creating or evaluating the irradiation plan parameter data set; and irradiating, with the particle beam and according to the irradiation plan parameter data set, the target volume in the irradiation volume.

21. A method for generating, by a computer, a plan parameter set of control parameters for controlling a radiation generating device so as to irradiate a target volume in an irradiation volume with an ion beam, wherein the target volume comprises a biological material, the method comprising:

a) providing a test parameter set of control parameters for controlling the radiation generating device;

b) determining a desired effective biological dose to be deposited in at least one sub-volume of the target volume;

c) determining a fluence and/or energy distribution of the ion beam within the target volume in the irradiation volume that corresponds to the test parameter set;

d) determining an effective biological dose distribution within the target volume that corresponds to the fluence and/or energy distribution, wherein an effective biological dose designates a dose deposited with photon beams that would produce a same effect as a dose deposited with ion beams produced using the test parameter set, wherein determining the effective biological dose distribution within the target volume that corresponds to the fluence and/or energy distribution comprises:

defining at least one sensitive volume within the biological material to be irradiated, determining, from the fluence and/or energy distribution of the ion beam, a microscopic dose distribution of the ion beam within the at least one sensitive volume, determining, from the microscopic dose distribution of the ion beam within the at least one sensitive volume, a spatial microscopic damage distribution of the ion beam in each of the sensitive volumes by using a first photon dose effect curve that describes a number of damage events per dose unit, determining, from the spatial microscopic damage distribution of the ion beam in each of the at least one sensitive volumes, an expected value of a number of correlated damage events in a sub-micrometer range in each of the at least one sensitive volumes, wherein correlated damage events are combinations of individual damage events within a specified distance, and determining, using the expected value of the number of correlated damage events in a sub-micrometer range in each of the at least one sensitive volumes, an effective biological dose of the ion beam in the biological material;

determining, using the effective biological dose of the ion beam in the biological material, the effective biological dose distribution of the ion beam in the target volume;

e) determining whether the desired effective biological dose to be deposited in the at least one sub-volume of the target volume is reached with the effective biological dose distribution within the target volume; and f) storing, as the plan parameter set of control parameters for controlling the radiation generating device, the test parameter set if the desired effective biological dose to be deposited in the at least one sub-volume of the target volume is reached with the effective biological dose distribution within the target volume or otherwise modifying the test parameter set and repeating steps b) through f) using the modified test parameter set.

* * * * *